United States Patent
Stewart et al.

(10) Patent No.: US 10,537,261 B2
(45) Date of Patent: Jan. 21, 2020

(54) REGION-OF-INTEREST REPRESENTATIONS FOR ELECTROANATOMICAL MAPPING

(71) Applicant: Boston Scientific Scimed Inc., Maple Grove, MN (US)

(72) Inventors: Brian Stewart, North Reading, MA (US); Doron Feinstein, Medford, MA (US); Mordechai Perlman, Cambridge, MA (US); Nathan H. Bennett, Cambridge, MA (US); Vasiliy E. Buharin, Cambridge, MA (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 0 days.

(21) Appl. No.: 15/975,588

(22) Filed: May 9, 2018

(65) Prior Publication Data
US 2018/0325401 A1 Nov. 15, 2018

Related U.S. Application Data

(60) Provisional application No. 62/504,301, filed on May 10, 2017.

(51) Int. Cl.
*A61B 5/044* (2006.01)
*G06T 17/20* (2006.01)
(Continued)

(52) U.S. Cl.
CPC .......... *A61B 5/044* (2013.01); *A61B 18/1492* (2013.01); *G06K 9/00523* (2013.01);
(Continued)

(58) Field of Classification Search
None
See application file for complete search history.

(56) References Cited

U.S. PATENT DOCUMENTS

| 6,070,094 A | 5/2000 | Swanson et al. |
| 6,233,491 B1 | 5/2001 | Kordis et al. |
(Continued)

OTHER PUBLICATIONS

International Search Report and Written Opinion issued in PCT/US2018/031884, dated Aug. 9, 2018, 13 pages.

*Primary Examiner* — Said Broome
(74) *Attorney, Agent, or Firm* — Faegre Baker Daniels LLP

(57) ABSTRACT

A system for facilitating display of cardiac information includes a display device configured to present a cardiac map; and a processing unit configured to: receive electrical signals and indications of measurement locations corresponding to the electrical signals; generate, based on the electrical signals, the cardiac map, which includes annotations representing cardiac signal features; and determine a set of interesting cardiac signal features. The processing unit also may determine, based on the set of interesting cardiac signal features, a region of interest; and facilitate display, via the display device, of the cardiac map and a representation of the region of interest. The representation of the region of interest includes a first display parameter value that is different from a second display parameter value, where the second display parameter value is associated with at least one cardiac signal feature that is not included within the region of interest.

19 Claims, 9 Drawing Sheets

(51) Int. Cl.
*G06T 19/20* (2011.01)
*G06K 9/32* (2006.01)
*G06K 9/00* (2006.01)
*G06T 7/11* (2017.01)
*A61B 18/14* (2006.01)
*A61B 18/00* (2006.01)

(52) U.S. Cl.
CPC .............. *G06K 9/3233* (2013.01); *G06T 7/11* (2017.01); *G06T 17/20* (2013.01); *G06T 19/20* (2013.01); *A61B 2018/0022* (2013.01); *A61B 2018/00267* (2013.01); *A61B 2018/00351* (2013.01); *A61B 2018/00577* (2013.01); *A61B 2018/00642* (2013.01); *G06T 2207/30048* (2013.01); *G06T 2219/004* (2013.01); *G06T 2219/2012* (2013.01)

(56) References Cited

U.S. PATENT DOCUMENTS

| | | | |
|---|---|---|---|
| 6,735,465 B2 | 5/2004 | Panescu | |
| 7,515,954 B2 | 4/2009 | Harlev et al. | |
| 8,103,338 B2 | 1/2012 | Harlev et al. | |
| 8,428,700 B2 | 4/2013 | Harlev et al. | |
| 8,615,287 B2 | 12/2013 | Harlev et al. | |
| 8,838,216 B2 | 9/2014 | Francis et al. | |
| 8,948,837 B2 | 2/2015 | Harlev et al. | |
| 2007/0167801 A1* | 7/2007 | Webler | G06T 19/00 600/459 |
| 2007/0299352 A1 | 12/2007 | Harlev et al. | |
| 2009/0069704 A1* | 3/2009 | MacAdam | A61B 5/044 600/523 |
| 2010/0002922 A1* | 1/2010 | Wiemker | G06T 7/0012 382/128 |
| 2014/0200874 A1* | 7/2014 | Zeng | G06T 19/20 703/11 |
| 2015/0065836 A1 | 3/2015 | Thakur et al. | |
| 2017/0120080 A1 | 5/2017 | Phillips et al. | |

* cited by examiner

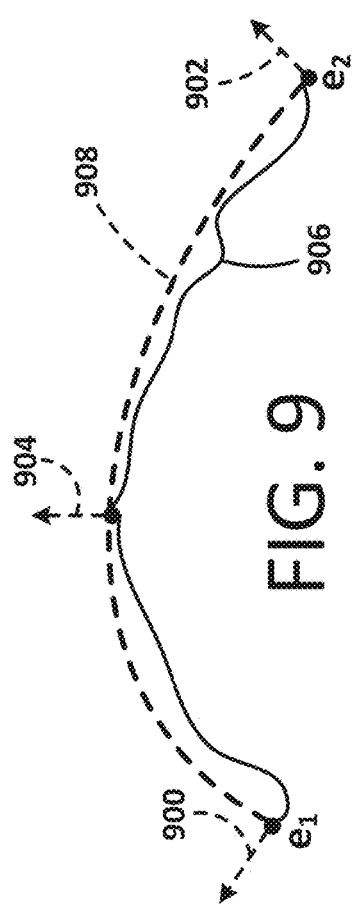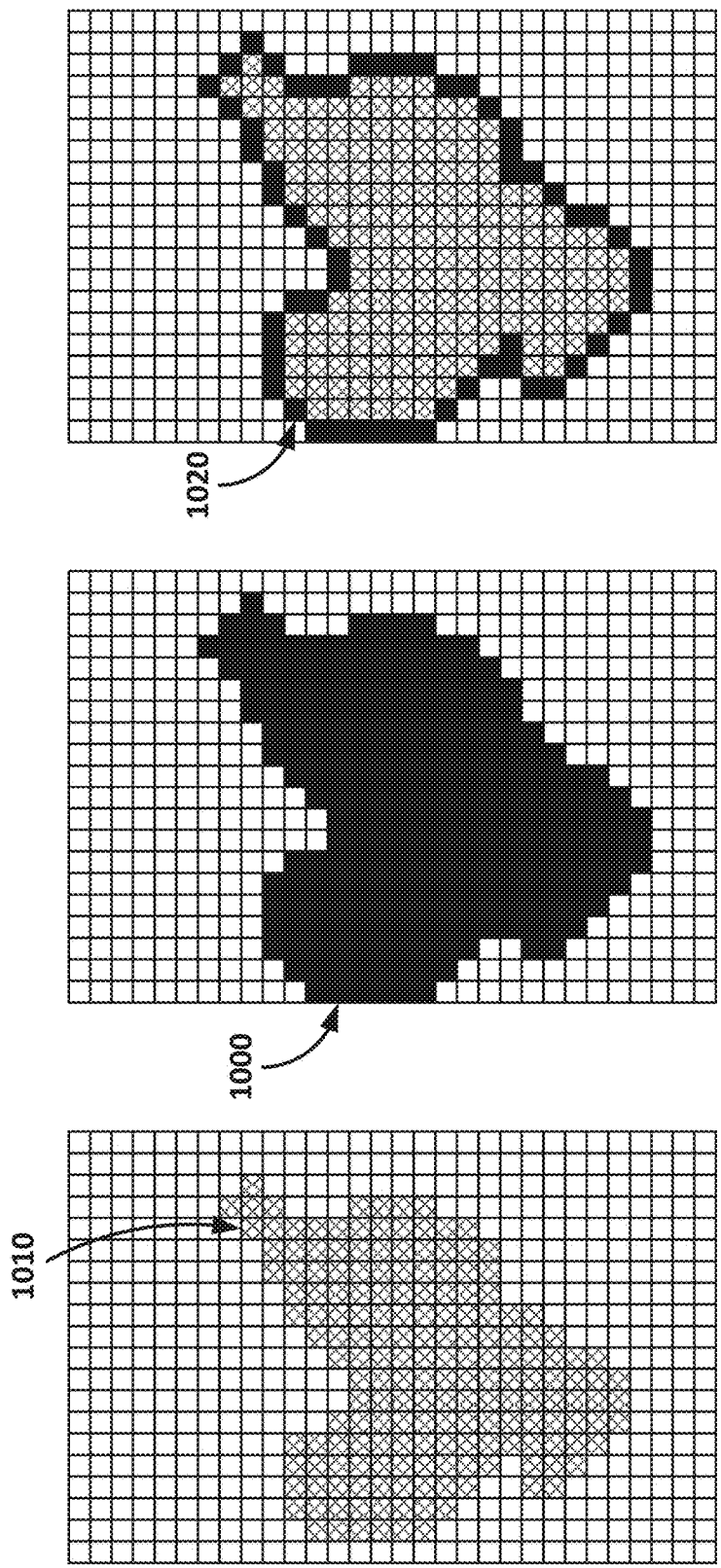

REGION-OF-INTEREST REPRESENTATIONS FOR ELECTROANATOMICAL MAPPING

CROSS-REFERENCE TO RELATED APPLICATION

This application claims priority to Provisional Application No. 62/504,301, filed May 10, 2017, which is herein incorporated by reference in its entirety.

TECHNICAL FIELD

The present disclosure relates to medical systems and methods for mapping an anatomical space of the body. More specifically, the disclosure relates to systems and methods for cardiac mapping.

BACKGROUND

Use of minimally invasive procedures, such as catheter ablation, to treat a variety of heart conditions, such as supraventricular and ventricular arrhythmias, is becoming increasingly more prevalent. Such procedures involve the mapping of electrical activity in the heart (e.g., based on cardiac signals), such as at various locations on the endocardium surface ("cardiac mapping"), to identify the site of origin of the arrhythmia followed by a targeted ablation of the site. To perform such cardiac mapping a catheter with one or more electrodes can be inserted into the patient's heart chamber.

Conventional three-dimensional (3D) mapping techniques include contact mapping and non-contact mapping, and may employ a combination of contact and non-contact mapping. In both techniques, one or more catheters are advanced into the heart. With some catheters, once in the chamber, the catheter may be deployed to assume a 3D shape. In contact mapping, physiological signals resulting from the electrical activity of the heart are acquired with one or more electrodes located at the catheter distal tip after determining that the tip is in stable and steady contact with the endocardium surface of a particular heart chamber. In non-contact-based mapping systems, using the signals detected by the non-contact electrodes and information on chamber anatomy and relative electrode location, the system provides physiological information regarding the endocardium of the heart chamber. Location and electrical activity is usually measured sequentially on a point-by-point basis at about 50 to 200 points on the internal surface of the heart to construct an electro-anatomical depiction of the heart. The generated map may then serve as the basis for deciding on a therapeutic course of action, for example, tissue ablation, to alter the propagation of the heart's electrical activity and to restore normal heart rhythm.

In many conventional mapping systems, the clinician visually inspects or examines the captured electrograms (EGMs), which increases examination time and cost. During an automatic electro-anatomical mapping process, however, approximately 6,000 to 20,000 intracardiac electrograms (EGMs) may be captured, which does not lend itself to being manually inspected in full by a clinician (e.g., a physician) for a diagnostic assessment, EGM categorization, and/or the like. Typically mapping systems extract scalar values from each EGM to construct voltage, activation, or other map types to depict overall patterns of activity within the heart. While maps typically are generated for entire heart chambers, much of the clinical focus is often placed on specific, smaller, regions such as, for example, isthmi, scars, lines of block, and/or the like. User-driven focus is typically poorly facilitated by mapping systems, and context-preserving methods largely rely on mental imaging, which is heavily operator-dependent. Additionally, context-lossy methods typically are not well tolerated by users and often result in procedural nuisance and delay. Furthermore, data-driven (algorithm-supported) focus is largely absent from conventional mapping systems.

SUMMARY

In an Example 1, a system for facilitating display of cardiac information, the system comprising: a display device configured to present a cardiac map; and a processing unit configured to: receive a plurality of electrical signals; receive an indication of a measurement location corresponding to each electrical signal of the plurality of electrical signals; generate, based on the plurality of electrical signals, the cardiac map, the cardiac map comprising a plurality of annotations representing a plurality of cardiac signal features; determine, from the plurality of cardiac signal features, a set of interesting cardiac signal features; determine, based on the set of interesting cardiac signal features, a region of interest; and facilitate display, via the display device, of the cardiac map and a representation of the region of interest, the representation of the region of interest comprising a first display parameter value that is different from a second display parameter value, wherein the second display parameter value is associated with at least one cardiac signal feature that is not included within the region of interest.

In an Example 2, the system of Example 1, wherein the processing unit is further configured to: determine, for each cardiac signal feature of the set of cardiac signal features, a radius of influence; and determine the region of interest based on the determined radius of influence for each cardiac signal feature.

In an Example 3, the system of Example 2, wherein the processing unit is configured to generate the cardiac map based on a mesh, and wherein the processing unit is further configured to: label each mesh vertex of a mesh element of the mesh with a first value; label each mesh vertex of the mesh element of the mesh with second value if a criterion is satisfied; and facilitate display of the representation of the region of interest based on the mesh vertex labels.

In an Example 4, the system of Example 3, wherein the mesh comprises a triangular mesh, wherein the first value comprises a 0, and wherein the second value comprises a 1, and wherein the processing unit is configured to: determine the number of mesh vertices of the mesh element that are labeled with the second value; apply a highlighting effect, but no border effect, to the mesh element if the number of mesh vertices of the mesh element that are labeled with the second value is 3; apply a border effect, but no highlighting effect, to the mesh element if the number of mesh vertices of the mesh element that are labeled with the second value is 2; and apply no border effect and no highlighting effect to the mesh element if the number of mesh vertices of the mesh element that are labeled with the second value is less than 2.

In an Example 5, the system of Example 2, wherein the processing unit is further configured to: determine a position of each model pixel; determine, for each model pixel, an influence subset of the set of interesting cardiac electrical signal features; determine, for each model pixel, an influence force associated with each cardiac electrical signal feature of the influence subset; determine, for each model pixel, a sum of the influence forces; compare, for each model pixel, the sum of the influence forces to a threshold; and apply a highlighting effect to each model pixel if the sum of the influence forces exceeds the threshold.

In an Example 6, the system of any of Examples 1-5, the cardiac electrical signal feature comprising at least one of an activation time, a detected activation, a minimum voltage value, a maximum voltages value, a maximum negative time-derivative of voltage, an instantaneous potential, a voltage amplitude, a dominant frequency, and a peak-to-peak voltage.

In an Example 7, the system of any of Examples 1-5, the display parameter comprising color saturation.

In an Example 8, a system for facilitating display of cardiac information, the system comprising: a display device configured to present a cardiac map; and a processing unit configured to: receive a plurality of electrical signals; receive an indication of a measurement location corresponding to each electrical signal of the plurality of electrical signals; generate, based on the plurality of electrical signals, the cardiac map, the cardiac map comprising a plurality of annotations representing a plurality of cardiac signal features; determine, from the plurality of cardiac signal features, a set of interesting cardiac signal features; determine, for each cardiac signal feature of the set of cardiac signal features, a radius of influence; determine, based on the set of interesting cardiac signal features and the corresponding radii of influence, a region of interest; and facilitate display, via the display device, of the cardiac map and a representation of the region of interest.

In an Example 9, the system of Example 8, the representation of the region of interest comprising a first color saturation value that is different from a second color saturation value, wherein the second color saturation value is associated with at least one cardiac signal feature that is not included within the region of interest.

In an Example 10, the system of either of Examples 8 or 9, the cardiac electrical signal feature comprising at least one of an activation time, a detected activation, a minimum voltage value, a maximum voltages value, a maximum negative time-derivative of voltage, an instantaneous potential, a voltage amplitude, a dominant frequency, and a peak-to-peak voltage.

In an Example 11, a method of presenting cardiac information, the method comprising: receiving a plurality of electrical signals; receiving an indication of a measurement location corresponding to each electrical signal of the plurality of electrical signals; generating, based on the plurality of electrical signals, the cardiac map, the cardiac map comprising a plurality of annotations representing a plurality of cardiac signal features; determining, from the plurality of cardiac signal features, a set of interesting cardiac signal features; determining, based on the set of interesting cardiac signal features, a region of interest; and facilitating display, via the display device, of the cardiac map and a representation of the region of interest, the representation of the region of interest comprising a first color saturation value that is different from a second color saturation value, wherein the second color saturation value is associated with at least one cardiac signal feature that is not included within the region of interest.

In an Example 12, the method of Example 11, further comprising: determining, for each cardiac signal feature of the set of cardiac signal features, a radius of influence; and determining the region of interest based on the determined radius of influence for each cardiac signal feature.

In an Example 13, the method of either of Examples 11 or 12, further comprising generating the cardiac map based on a mesh, and wherein the method further comprises: labeling each mesh vertex of a mesh element of the mesh with a first value; labeling each mesh vertex of the mesh element of the mesh with second value if a criterion is satisfied; and facilitating display of the representation of the region of interest based on the mesh vertex labels.

In an Example 14, the method of Example 12, further comprising: determining a position of each model pixel; determining, for each model pixel, an influence subset of the set of interesting cardiac electrical signal features; determining, for each model pixel, an influence force associated with each cardiac electrical signal feature of the influence subset; determining, for each model pixel, a sum of the influence forces; comparing, for each model pixel, the sum of the influence forces to a threshold; and applying a highlighting effect to each model pixel if the sum of the influence forces exceeds the threshold.

In an Example 15, the method of any of Examples 11-14, the cardiac electrical signal feature comprising at least one of an activation time, a detected activation, a minimum voltage value, a maximum voltages value, a maximum negative time-derivative of voltage, an instantaneous potential, a voltage amplitude, a dominant frequency, and a peak-to-peak voltage.

In an Example 16, a system for facilitating display of cardiac information, the system comprising: a display device configured to present a cardiac map; and a processing unit configured to: receive a plurality of electrical signals; receive an indication of a measurement location corresponding to each electrical signal of the plurality of electrical signals; generate, based on the plurality of electrical signals, the cardiac map, the cardiac map comprising a plurality of annotations representing a plurality of cardiac signal features; determine, from the plurality of cardiac signal features, a set of interesting cardiac signal features; determine, based on the set of interesting cardiac signal features, a region of interest; and facilitate display, via the display device, of the cardiac map and a representation of the region of interest, the representation of the region of interest comprising a first color saturation value that is different from a second color saturation value, wherein the second color saturation value is associated with at least one cardiac signal feature that is not included within the region of interest.

In an Example 17, the system of Example 16, wherein the processing unit is further configured to: determine, for each cardiac signal feature of the set of cardiac signal features, a radius of influence; and determine the region of interest based on the determined radius of influence for each cardiac signal feature.

In an Example 18, the system of Example 17, wherein the processing unit is configured to generate the cardiac map based on a mesh, and wherein the processing unit is further configured to: label each mesh vertex of a mesh element of the mesh with a first value; label each mesh vertex of the mesh element of the mesh with second value if a criterion is satisfied; and facilitate display of the representation of the region of interest based on the mesh vertex labels.

In an Example 19, the system of Example 18, wherein the mesh comprises a triangular mesh, wherein the first value comprises a 0, and wherein the second value comprises a 1, and wherein the processing unit is configured to: determine the number of mesh vertices of the mesh element that are labeled with the second value; apply a highlighting effect, but no border effect, to the mesh element if the number of mesh vertices of the mesh element that are labeled with the second value is 3; apply a border effect, but no highlighting effect, to the mesh element if the number of mesh vertices of the mesh element that are labeled with the second value is 2; and apply no border effect and no highlighting effect to the mesh element if the number of mesh vertices of the mesh element that are labeled with the second value is less than 2.

In an Example 20, the system of Example 17, wherein the processing unit is further configured to: determine a position of each model pixel; determine, for each model pixel, an influence subset of the set of interesting cardiac electrical signal features; determine, for each model pixel, an influence force associated with each cardiac electrical signal feature of the influence subset; determine, for each model pixel, a sum of the influence forces; compare, for each model pixel, the sum of the influence forces to a threshold; and apply a highlighting effect to each model pixel if the sum of the influence forces exceeds the threshold.

In an Example 21, the system of Example 20, the representation of the region of interest comprising a border, wherein the processing unit is further configured to: generate a scaled region of interest shape corresponding to the region of interest; and generate the border by facilitating display of the highlighted pixels above the scaled region of interest shape.

In an Example 22, the system of Example 16, the cardiac electrical signal feature comprising at least one of an activation time, a detected activation, a minimum voltage value, a maximum voltages value, a maximum negative time-derivative of voltage, an instantaneous potential, a voltage amplitude, a dominant frequency, and a peak-to-peak voltage.

In an Example 23, a system for facilitating display of cardiac information, the system comprising: a display device configured to present a cardiac map; and a processing unit configured to: receive a plurality of electrical signals; receive an indication of a measurement location corresponding to each electrical signal of the plurality of electrical signals; generate, based on the plurality of electrical signals, the cardiac map, the cardiac map comprising a plurality of annotations representing a plurality of cardiac signal features; determine, from the plurality of cardiac signal features, a set of interesting cardiac signal features; determine, for each cardiac signal feature of the set of cardiac signal features, a radius of influence; determine, based on the set of interesting cardiac signal features and the corresponding radii of influence, a region of interest; and facilitate display, via the display device, of the cardiac map and a representation of the region of interest.

In an Example 24, the system of Example 23, the representation of the region of interest comprising a first color saturation value that is different from a second color saturation value, wherein the second color saturation value is associated with at least one cardiac signal feature that is not included within the region of interest.

In an Example 25, the system of Example 23, wherein the processing unit is configured to generate the cardiac map based on a mesh, and wherein the processing unit is further configured to: label each mesh vertex of a mesh element of the mesh with a first value; label each mesh vertex of the mesh element of the mesh with second value if a criterion is satisfied; and facilitate display of the representation of the region of interest based on the mesh vertex labels.

In an Example 26, the system of Example 25, wherein the mesh comprises a triangular mesh, wherein the first value comprises a 0, and wherein the second value comprises a 1, and wherein the processing unit is configured to: determine the number of mesh vertices of the mesh element that are labeled with the second value; apply a highlighting effect, but no border effect, to the mesh element if the number of mesh vertices of the mesh element that are labeled with the second value is 3; apply a border effect, but no highlighting effect, to the mesh element if the number of mesh vertices of the mesh element that are labeled with the second value is 2; and apply no border effect and no highlighting effect to the mesh element if the number of mesh vertices of the mesh element that are labeled with the second value is less than 2.

In an Example 27, the system of Example 23, wherein the processing unit is further configured to: determine a position of each model pixel; determine, for each model pixel, an influence subset of the set of interesting cardiac electrical signal features; determine, for each model pixel, an influence force associated with each cardiac electrical signal feature of the influence subset; determine, for each model pixel, a sum of the influence forces; compare, for each model pixel, the sum of the influence forces to a threshold; and apply a highlighting effect to each model pixel if the sum of the influence forces exceeds the threshold.

In an Example 28, the system of Example 23, the cardiac electrical signal feature comprising at least one of an activation time, a detected activation, a minimum voltage value, a maximum voltages value, a maximum negative time-derivative of voltage, an instantaneous potential, a voltage amplitude, a dominant frequency, and a peak-to-peak voltage.

In an Example 29, a method of presenting cardiac information, the method comprising: receiving a plurality of electrical signals; receiving an indication of a measurement location corresponding to each electrical signal of the plurality of electrical signals; generating, based on the plurality of electrical signals, the cardiac map, the cardiac map comprising a plurality of annotations representing a plurality of cardiac signal features; determining, from the plurality of cardiac signal features, a set of interesting cardiac signal features; determining, based on the set of interesting cardiac signal features, a region of interest; and facilitating display, via the display device, of the cardiac map and a representation of the region of interest, the representation of the region of interest comprising a first color saturation value that is different from a second color saturation value, wherein the second color saturation value is associated with at least one cardiac signal feature that is not included within the region of interest.

In an Example 30, the method of Example 29, further comprising: determining, for each cardiac signal feature of the set of cardiac signal features, a radius of influence; and determining the region of interest based on the determined radius of influence for each cardiac signal feature.

In an Example 31, the method of Example 29, further comprising generating the cardiac map based on a mesh, and wherein the method further comprises: labeling each mesh vertex of a mesh element of the mesh with a first value; labeling each mesh vertex of the mesh element of the mesh with second value if a criterion is satisfied; and facilitating display of the representation of the region of interest based on the mesh vertex labels.

In an Example 32, the method of Example 31, wherein the mesh comprises a triangular mesh, wherein the first value comprises a 0, and wherein the second value comprises a 1, the method further comprising: determining the number of mesh vertices of the mesh element that are labeled with the second value; applying a highlighting effect, but no border effect, to the mesh element if the number of mesh vertices of the mesh element that are labeled with the second value is 3; applying a border effect, but no highlighting effect, to the mesh element if the number of mesh vertices of the mesh element that are labeled with the second value is 2; and applying no border effect and no highlighting effect to the mesh element if the number of mesh vertices of the mesh element that are labeled with the second value is less than 2.

In an Example 33, the method of Example 29, further comprising: determining a position of each model pixel; determining, for each model pixel, an influence subset of the set of interesting cardiac electrical signal features; determining, for each model pixel, an influence force associated with each cardiac electrical signal feature of the influence subset; determining, for each model pixel, a sum of the influence forces; comparing, for each model pixel, the sum of the influence forces to a threshold; and applying a highlighting effect to each model pixel if the sum of the influence forces exceeds the threshold.

In an Example 34, the method of Example 33, the representation of the region of interest comprising a border, wherein the processing unit is further configured to: generate a scaled region of interest shape corresponding to the region of interest; and generate the border by facilitating display of the highlighted pixels above the scaled region of interest shape.

In an Example 35, the method of Example 29, the cardiac electrical signal feature comprising at least one of an activation time, a detected activation, a minimum voltage value, a maximum voltages value, a maximum negative time-derivative of voltage, an instantaneous potential, a voltage amplitude, a dominant frequency, and a peak-to-peak voltage.

While multiple embodiments are disclosed, still other embodiments of the presently disclosed subject matter will become apparent to those skilled in the art from the following detailed description, which shows and describes illustrative embodiments of the disclosed subject matter. Accordingly, the drawings and detailed description are to be regarded as illustrative in nature and not restrictive.

BRIEF DESCRIPTION OF THE DRAWINGS

FIG. 9 is a conceptual schematic diagram depicting an illustrative example of generating a representation of a region of interest, using aspects of embodiments of the method depicted in FIG. 8, in accordance with embodiments of the subject matter disclosed herein.

FIGS. 10A-10C are conceptual schematic diagrams depicting an illustrative example of generating a border of a representation of a region of interest, in accordance with embodiments of the subject matter disclosed herein.

Figure 1:
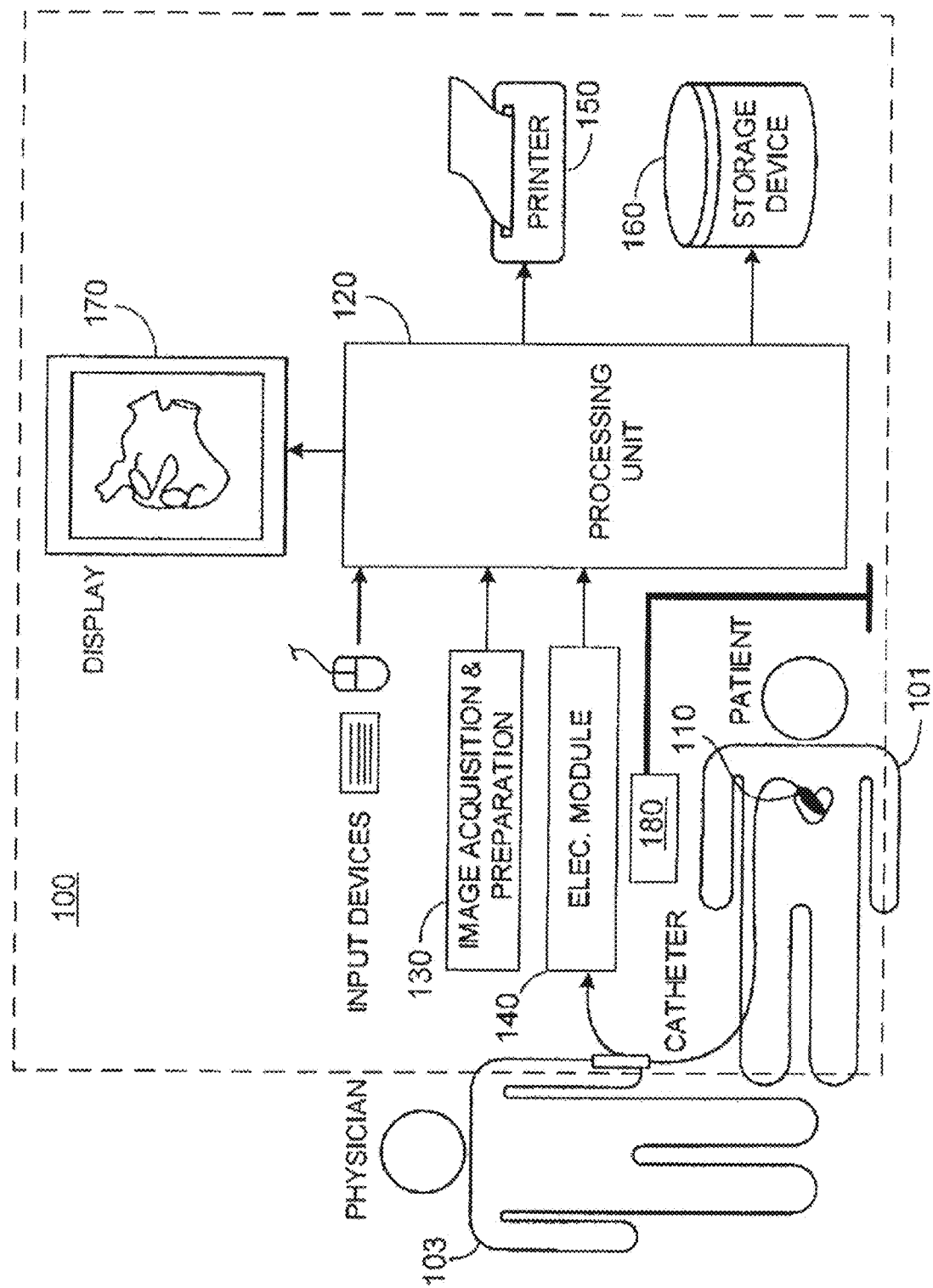
FIG. 1 is a conceptual schematic diagram depicting an illustrative cardiac mapping system, in accordance with embodiments of the subject matter disclosed herein.

While the disclosed subject matter is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure as defined by the appended claims.

As the terms are used herein with respect to measurements (e.g., dimensions, characteristics, attributes, components, etc.), and ranges thereof, of tangible things (e.g., products, inventory, etc.) and/or intangible things (e.g., data, electronic representations of currency, accounts, information, portions of things (e.g., percentages, fractions), calculations, data models, dynamic system models, algorithms, parameters, etc.), "about" and "approximately" may be used, interchangeably, to refer to a measurement that includes the stated measurement and that also includes any measurements that are reasonably close to the stated measurement, but that may differ by a reasonably small amount such as will be understood, and readily ascertained, by individuals having ordinary skill in the relevant arts to be attributable to measurement error; differences in measurement and/or manufacturing equipment calibration; human error in reading and/or setting measurements; adjustments made to optimize performance and/or structural parameters in view of other measurements (e.g., measurements associated with other things); particular implementation scenarios; imprecise adjustment and/or manipulation of things, settings, and/or measurements by a person, a computing device, and/or a machine; system tolerances; control loops; machine-learning; foreseeable variations (e.g., statistically insignificant variations, chaotic variations, system and/or model instabilities, etc.); preferences; and/or the like.

Although the term "block" may be used herein to connote different elements illustratively employed, the term should not be interpreted as implying any requirement of, or particular order among or between, various blocks disclosed herein. Similarly, although illustrative methods may be represented by one or more drawings (e.g., flow diagrams, communication flows, etc.), the drawings should not be interpreted as implying any requirement of, or particular order among or between, various steps disclosed herein. However, certain embodiments may require certain steps and/or certain orders between certain steps, as may be explicitly described herein and/or as may be understood from the nature of the steps themselves (e.g., the performance of some steps may depend on the outcome of a previous step). Additionally, a "set," "subset," or "group" of items (e.g., inputs, algorithms, data values, etc.) may include one or more items, and, similarly, a subset or subgroup of items may include one or more items. A "plurality" means more than one.

As used herein, the term "based on" is not meant to be restrictive, but rather indicates that a determination, identification, prediction, calculation, and/or the like, is performed by using, at least, the term following "based on" as an input.

For example, predicting an outcome based on a particular piece of information may additionally, or alternatively, base the same determination on another piece of information.

DETAILED DESCRIPTION

Embodiments of systems and methods described herein facilitate processing sensed cardiac electrical signals to present a representation of a region of interest (ROI) on an electroanatomical map. In embodiments, representations of ROIs may facilitate clear visual distinction of the ROI while preserving the context of the annotations. Representations of ROIs may include highlighting effects applied to a map that are persistent, tolerant to view angles, tolerant to various zoom levels, and do not obstruct other information in the map. In embodiments, for example, a representation of an ROI may include a bordered, highlighted overlay of a corresponding portion of the surface of the map on top of a de-saturated map. In embodiments, rendering representations of ROIs with borders may facilitate clearly presenting multiple distinct ROIs (which may, in embodiments, be referred to as multiple portions of an ROI). Embodiments of the highlighting operations described herein may be user driven and/or algorithm driven.

According to embodiments, to perform aspects of embodiments of the methods described herein, cardiac electrical signals may be obtained from a mapping catheter (e.g., associated with a mapping system), a recording system, a coronary sinus (CS) catheter or other reference catheter, an ablation catheter, a memory device (e.g., a local memory, a cloud server, etc.), a communication component, a medical device (e.g., an implantable medical device, an external medical device, a telemetry device, etc.), and/or the like.

As the term is used herein, a sensed cardiac electrical signal may refer to one or more sensed signals. Each cardiac electrical signal may include a number of intracardiac electrograms (EGMs) sensed within a patient's heart, and may include any number of features that may be ascertained by aspects of the system 100. Examples of cardiac electrical signal features include, but are not limited to, activation times, activations, activation waveforms, filtered activation waveforms, minimum voltage values, maximum voltages values, maximum negative time-derivatives of voltages, instantaneous potentials, voltage amplitudes, dominant frequencies, peak-to-peak voltages, and/or the like. A cardiac electrical signal feature may refer to one or more features extracted from one or more cardiac electrical signals, derived from one or more features that are extracted from one or more cardiac electrical signals, and/or the like. Additionally, a representation, on a cardiac and/or a surface map, of a cardiac electrical signal feature may represent one or more cardiac electrical signal features, an interpolation of a number of cardiac electrical signal features, and/or the like.

Each cardiac signal also may be associated with a set of respective position coordinates that corresponds to the location at which the cardiac electrical signal was sensed. Each of the respective position coordinates for the sensed cardiac signals may include three-dimensional Cartesian coordinates, polar coordinates, and/or the like. In embodiments, other coordinate systems can be used. In embodiments, an arbitrary origin is used and the respective position coordinates refer to positions in space relative to the arbitrary origin. Since, in embodiments, the cardiac signals may be sensed on the cardiac surfaces, the respective position coordinates may be on the endocardial surface, epicardial surface, in the mid-myocardium of the patient's heart, and/or in the vicinity of one of one of these.

FIG. 1 shows a schematic diagram of an exemplary embodiment of a cardiac mapping system 100. As indicated above, embodiments of the subject matter disclosed herein may be implemented in a mapping system (e.g., the mapping system 100), while other embodiments may be implemented in an ablation system, a recording system, a computer analysis system, and/or the like. The mapping system 100 includes a moveable catheter 110 having multiple spatially distributed electrodes. During a signal-acquisition stage of a cardiac mapping procedure, the catheter 110 is displaced to multiple locations within the heart chamber into which the catheter 110 is inserted. In some embodiments the distal end of the catheter 110 is fitted with multiple electrodes spread somewhat uniformly over the catheter. For example, the electrodes may be mounted on the catheter 110 following a 3D olive shape, a basket shape, and/or the like. The electrodes are mounted on a device capable of deploying the electrodes into the desired shape while inside the heart, and retracting the electrodes when the catheter is removed from the heart. To allow deployment into a 3D shape in the heart, electrodes may be mounted on a balloon, shape memory material such as Nitinol, actuable hinged structure, and/or the like. According to embodiments, the catheter 110 may be a mapping catheter, an ablation catheter, a diagnostic catheter, a CS catheter, and/or the like. For example, aspects of embodiments of the catheter 110, the electrical signals obtained using the catheter 110, and subsequent processing of the electrical signals, as described herein, may also be applicable in implementations having a recording system, ablation system, and/or any other system having a catheter with electrodes that may be configured to obtain cardiac electrical signals.

At each of the locations to which the catheter 110 is moved, the catheter's multiple electrodes acquire signals resulting from the electrical activity in the heart. Consequently, reconstructing and presenting to a user (such as a doctor and/or technician) physiological data pertaining to the heart's electrical activity may be based on information acquired at multiple locations, thereby providing a more accurate and faithful reconstruction of physiological behavior of the endocardium surface. The acquisition of signals at multiple catheter locations in the heart chamber enables the catheter to effectively act as a "mega-catheter" whose effective number of electrodes and electrode span is proportional to the product of the number of locations in which signal acquisition is performed and the number of electrodes the catheter has.

To enhance the quality of the reconstructed physiological information at the endocardium surface, in some embodiments the catheter 110 is moved to more than three locations (for example, more than 5, 10, or even 50 locations) within the heart chamber. Further, the spatial range over which the catheter is moved may be larger than one third (⅓) of the diameter of the heart cavity (for example, larger than 35%, 40%, 50% or even 60% of the diameter of the heart cavity). Additionally, in some embodiments the reconstructed physiological information is computed based on signals measured over several heart beats, either at a single catheter location within the heart chamber or over several locations. In circumstances where the reconstructed physiological information is based on multiple measurements over several heart beats, the measurements may be synchronized with one another so that the measurement are performed at approximately the same phase of the heart cycle. The signal measurements over multiple beats may be synchronized based on features detected from physiological data such as surface electrocardiograms (ECGs) and/or intracardiac electrograms (EGMs).

The cardiac mapping system 100 further includes a processing unit 120 which performs several of the operations pertaining to the mapping procedure, including the reconstruction procedure to determine the physiological information at the endocardium surface (e.g., as described above) and/or within a heart chamber. The processing unit 120 also may perform a catheter registration procedure. The processing unit 120 also may generate a 3D grid used to aggregate the information captured by the catheter 110 and to facilitate display of portions of that information.

The location of the catheter 110 inserted into the heart chamber can be determined using a conventional sensing and tracking system 180 that provides the 3D spatial coordinates of the catheter and/or its multiple electrodes with respect to the catheter's coordinate system as established by the sensing and tracking system. These 3D spatial locations may be used in building the 3D grid. Embodiments of the system 100 may use a hybrid location technology that combines impedance location with magnetic location technology. This combination may enable the system 100 to accurately track catheters that are connected to the system 100. Magnetic location technology uses magnetic fields generated by a localization generator positioned under the patient table to track catheters with magnetic sensors. Impedance location technology may be used to track catheters that may not be equipped with a magnetic location sensor, and may utilize surface ECG patches.

In embodiments, to perform a mapping procedure and reconstruct physiological information on the endocardium surface, the processing unit 120 may align the coordinate system of the catheter 110 with the endocardium surface's coordinate system. The processing unit 110 (or some other processing component of the system 100) may determine a coordinate system transformation function that transforms the 3D spatial coordinates of the catheter's locations into coordinates expressed in terms of the endocardium surface's coordinate system, and/or vice-versa. In embodiments, such a transformation may not be necessary, as embodiments of the 3D grid described herein may be used to capture contact and non-contact EGMs, and select mapping values based on statistical distributions associated with nodes of the 3D grid. The processing unit 120 also may perform post-processing operations on the physiological information to extract and display useful features of the information to the operator of the system 100 and/or other persons (e.g., a physician).

According to embodiments, the signals acquired by the multiple electrodes of catheter 110 are passed to the processing unit 120 via an electrical module 140, which may include, for example, a signal conditioning component. The electrical module 140 may be configured to receive the signals communicated from the catheter 110 and perform signal enhancement operations on the signals before they are forwarded to the processing unit 120. The electrical module 140 may include signal conditioning hardware, software, and/or firmware that may be used to amplify, filter and/or sample intracardiac potential measured by one or more electrodes. The intracardiac signals typically have a maximum amplitude of 60 mV, with a mean of a few millivolts.

In some embodiments the signals are bandpass filtered in a frequency range (e.g., 0.5-500 Hz) and sampled with analog to digital converters (e.g., with 15-bit resolution at 1 kHz). To avoid interference with electrical equipment in the room, the signal may be filtered to remove the frequency corresponding to the power supply (e.g., 60 Hz). Other types of signal processing operations such as spectral equalization, automatic gain control, etc. may also take place. For example, in embodiments, the intracardiac signals may be unipolar signals, measured relative to a reference (which may be a virtual reference) such as, for example, a coronary sinus catheter or Wilson's Central Terminal (WCT), from which the signal processing operations may compute differences to generate multipolar signals (e.g., bipolar signals, tripolar signals, etc.). The signals may be otherwise processed (e.g., filtered, sampled, etc.) before and/or after generating the multipolar signals. The resultant processed signals are forwarded by the module 140 to the processing unit 120 for further processing.

In embodiments, the processing unit 120 may be configured to process the resultant processed signals. In embodiments, because the processing unit 120 may be configured to process any number of different types of electrical signals, whether they have been preprocessed or not, the terms "electrical signal(s)," "cardiac electrical signal(s)" and terms including one or more of the aforementioned, shall be understood to refer to electrical signals, processed (e.g., "pre-processed") electrical signals, raw signal data, interpolated electrical signals, estimated electrical signals, and/or any other type of information representing an electrical signal, as described herein.

Embodiments of the processing unit 120 may be configured to receive a number of electrical signals such as, for example, cardiac electrical signals. The processing unit 120 may receive the electrical signals from the electrical module 140, from a memory device, from a catheter (e.g., the catheter 110), from another computing device, from a user via a user input device, and/or the like. In embodiments, the processing unit 120 may receive an indication of a measurement location corresponding to each electrical signal. The processing unit 120 may be configured to generate, based on the electrical signals, a cardiac map, which may be presented via a display device 170. In embodiments, the cardiac map includes a number of annotations representing a number of cardiac signal features, which may include, for example, one or more activation times, minimum voltage values, maximum voltage values, maximum negative time-derivatives of voltage, instantaneous potentials, voltage amplitudes, dominant frequencies, and/or peak-to-peak voltages.

The processing unit 120 may be further configured to determine, from the cardiac signal features, a set of interesting cardiac signal features. According to embodiments, an "interesting" cardiac signal feature is a cardiac signal feature that has been designated as such, such as, for example, via user input, an automatic algorithm, and/or the like. The processing unit 120 may also be configured to determine, based on the set of interesting cardiac signal features, a region of interest (ROI). In embodiments, an ROI refers to a set of information that is designated as interesting, and may, in embodiments be determined based on another set of information designated as interesting. That is, for example, the processing unit 120 may be configured to determine (e.g., based on user input, an algorithm, etc.) a set of interesting electrical signal features (e.g., a set of information that is designated as interesting) and, based on the set of interesting signal features, a region of interest (e.g., another set of information that is designated as interesting). In embodiments, a region of interest may refer to a set of mapped data points such as, for example, a set of data points that are mapped, using a mesh, to an electroanatomical shell surface (e.g., a cardiac model). A region of interest may include the set of interesting cardiac signal features, information associated with the set of interesting cardiac signal features, and/or the like.

According to embodiments, the processing unit 120 may be configured to facilitate display, via a display device 170, of the cardiac map and a representation of the region of interest. The representation of the region of interest may include, for example, a first display parameter value that is different from a second display parameter value. In embodiments, the display parameter may include any number of different types of parameters, settings, and/or the like that may be configured to change one or more features of an appearance of a displayed representation. For example, in embodiments, display parameters may include brightness, contrast, color saturation, sharpness, and/or the like. Thus, in embodiments, the representation of the region of interest may include a first color saturation value that is different from a second color saturation value, where the second color saturation value is associated with at least one cardiac signal feature that is not included within the region of interest. Color saturation values, relative color saturation values, and/or the like, may be adjustable via user input, an algorithm, and/or the like.

As further shown in FIG. 1, the cardiac mapping system 100 also may include peripheral devices such as a printer 150 and/or display device 170, both of which may be interconnected to the processing unit 120. Additionally, the mapping system 100 includes storage device 160 that may be used to store data acquired by the various interconnected modules, including the volumetric images, raw data measured by electrodes and/or the resultant endocardium representation computed therefrom, the partially computed transformations used to expedite the mapping procedures, the reconstructed physiological information corresponding to the endocardium surface, and/or the like.

In embodiments, the processing unit 120 may be configured to automatically improve the accuracy of its algorithms by using one or more artificial intelligence (i.e., machine-learning) techniques, classifiers, and/or the like. In embodiments, for example, the processing unit may use one or more supervised and/or unsupervised techniques such as, for example, support vector machines (SVMs), k-nearest neighbor techniques, artificial neural networks, and/or the like. In embodiments, classifiers may be trained and/or adapted using feedback information from a user, other metrics, and/or the like.

The illustrative cardiac mapping system 100 shown in FIG. 1 is not intended to suggest any limitation as to the scope of use or functionality of embodiments of the present disclosure. Neither should the illustrative cardiac mapping system 100 be interpreted as having any dependency or requirement related to any single component or combination of components illustrated therein. Additionally, various components depicted in FIG. 1 may be, in embodiments, integrated with various ones of the other components depicted therein (and/or components not illustrated), all of which are considered to be within the ambit of the subject matter disclosed herein. For example, the electrical module 140 may be integrated with the processing unit 120. Additionally, or alternatively, aspects of embodiments of the cardiac mapping system 100 may be implemented in a computer analysis system configured to receive cardiac electrical signals and/or other information from a memory device (e.g., a cloud server, a mapping system memory, etc.), and perform aspects of embodiments of the methods described herein for processing cardiac information (e.g., determining annotation waveforms, etc.). That is, for example, a computer analysis system may include a processing unit 120, but not a mapping catheter.

Figure 2:
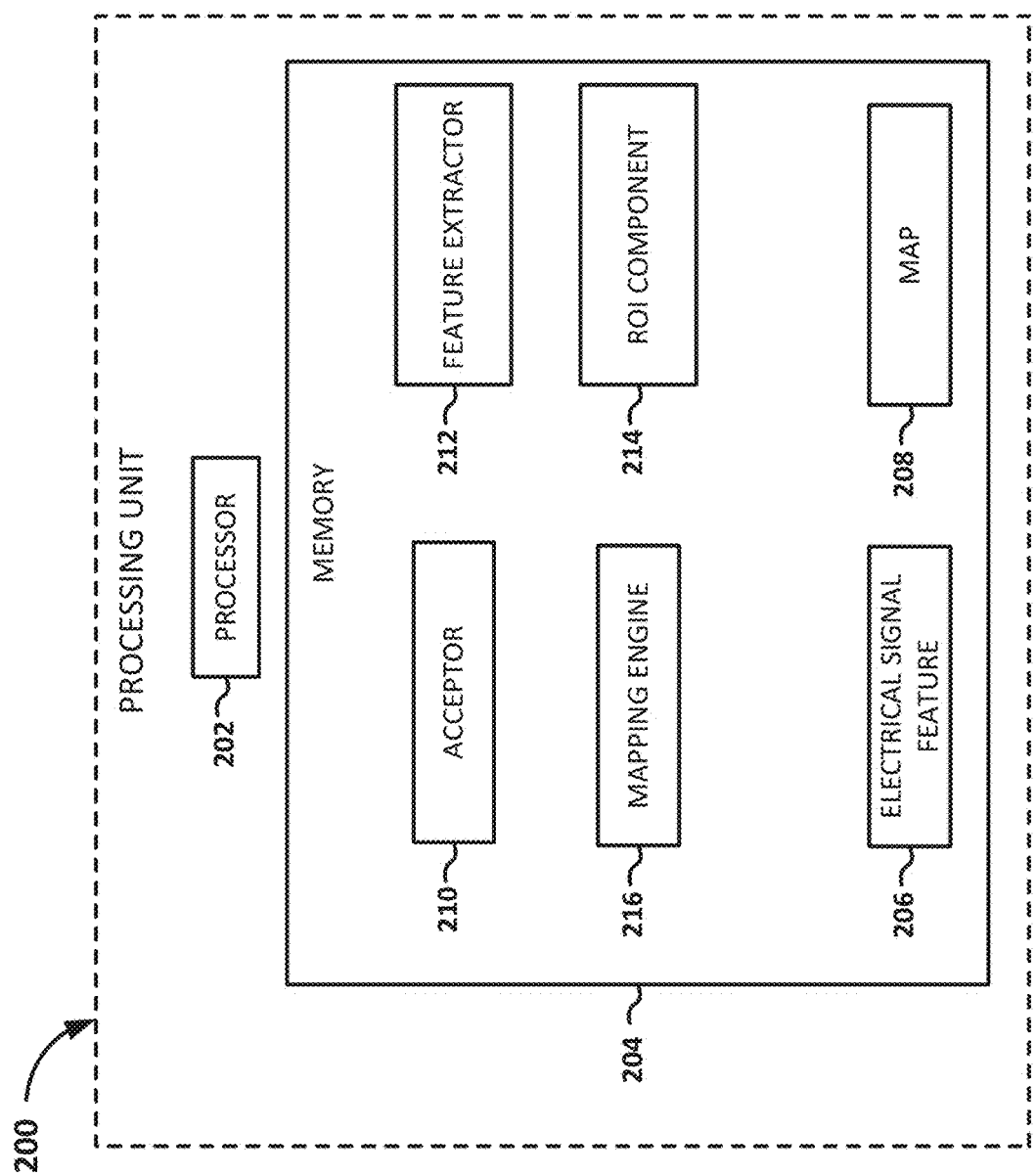
FIG. 2 is a block diagram depicting an illustrative processing unit, in accordance with embodiments of the subject matter disclosed herein.

FIG. 2 is a block diagram of an illustrative processing unit 200, in accordance with embodiments of the disclosure. The processing unit 200 may be, be similar to, include, or be included in the processing unit 120 depicted in FIG. 1. As shown in FIG. 2, the processing unit 200 may be implemented on a computing device that includes a processor 202 and a memory 204. Although the processing unit 200 is referred to herein in the singular, the processing unit 200 may be implemented in multiple instances (e.g., as a server cluster), distributed across multiple computing devices, instantiated within multiple virtual machines, and/or the like. One or more components for facilitating cardiac mapping may be stored in the memory 204. In embodiments, the processor 202 may be configured to instantiate the one or more components to generate one or more electrical signal features 206 and a cardiac map 208, either of which may be stored in the memory 204.

As is further depicted in FIG. 2, the processing unit 200 may include an acceptor 210 configured to receive electrical signals. The acceptor 210 may be configured to receive electrical signals from a mapping catheter (e.g., the mapping catheter 110 depicted in FIG. 1), a memory device (e.g., the memory 204), a server, and/or the like. The measured electrical signals may include a number of intracardiac electrograms (EGMs) sensed within a patient's heart. The acceptor 210 may also receive an indication of a measurement location corresponding to each of the electrical signals. In embodiments, the acceptor 210 may be configured to determine whether to accept the electrical signals that have been received. The acceptor 210 may utilize any number of different components and/or techniques to determine which electrical signals or beats to accept, such as filtering, beat matching, morphology analysis, positional information (e.g., catheter motion), respiration gating, and/or the like.

The accepted electrical signals are received by a feature extractor 212 that is configured to extract at least one electrical signal feature from each of the electrical signals. In embodiments, an extracted electrical signal feature may be used to annotate a cardiac map, in which case, the extracted electrical signal feature may be referred to, interchangeably, as an annotation feature. In embodiments in which the electrical signal is a cardiac electrical signal, an extracted signal feature may be referred to, interchangeably, as a cardiac electrical signal feature. In embodiments, the at least one electrical signal feature includes at least one value corresponding to at least one annotation metric. The at least one feature may include at least one event, where the at least one event includes the at least one value corresponding to the at least one metric and/or at least one corresponding time (a corresponding time does not necessarily exist for each annotation feature). According to embodiments, the at least one electrical signal feature may include, for example, an activation time, detected activation (e.g., a component of an activation waveform), activation waveform, activation histogram, minimum voltage value, maximum voltage value, maximum negative time-derivative of voltage, an instantaneous potential, a voltage amplitude, a dominant frequency, a peak-to-peak voltage, an activation duration, an annotation waveform (e.g., an activation waveform), and/or the like. A cardiac electrical signal feature may refer to one or more features extracted from one or more cardiac electrical signals, derived from one or more features that are extracted from one or more cardiac electrical signals, and/or the like. Additionally, a representation, on a cardiac and/or a surface map, of a cardiac electrical signal feature may represent one or more cardiac electrical signal features, an interpolation of a number of cardiac electrical signal features, and/or the like.

According to embodiments, feature extractor 212 may be configured to detect specified events (e.g., activations) and to generate an annotation waveform (a type of electrical signal feature 206), which may be, for example, an activation waveform. An annotation waveform is a set of annotation waveform values and may include, for example, a set of discrete activation annotation values (e.g., a set of annotation waveform values, a set of time annotations, etc.), a function defining an annotation waveform curve, and/or the like. Accordingly, in embodiments, the term "annotation waveform" may include a "filtered annotation waveform." An activation waveform is a set of activation waveform values and may include, for example, a set of discrete activation waveform values (e.g., a set of activation waveform values, a set of activation time annotations, etc.), a function defining an activation waveform curve, and/or the like. Accordingly, in embodiments, the term "activation waveform" may include a "filtered activation waveform."

According to embodiments, the feature extractor 212 may be, include, be similar to, or be included in, aspects of embodiments of the annotation waveform generator described in U.S. Application No. 62/486,926, filed on Apr. 18, 2017, entitled "ANNOTATION WAVEFORM;" U.S. Application No. 62/486,909, filed on Apr. 18, 2017, entitled "ELECTROANATOMICAL MAPPING TOOLS FACILITATED BY ACTIVATION WAVEFORMS;" and/or U.S. Application No. 62/486,920, filed on Apr. 18, 2017, entitled "ANNOTATION HISTOGRAM;" the entirety of each of which is hereby incorporated by reference herein for all purposes. In embodiments, the feature extractor 212 may be configured to generate an annotation histogram (another type of electrical signal feature 206) having a number of bins within which annotations from electrograms (EGMs) are included. The feature extractor 212 may be configured to aggregate a set of annotation features by including each of the features and/or EGMs in a histogram. For example, the feature extractor 212 may be configured to aggregate the set of activation features by assigning a confidence level to each event corresponding to an activation feature; determining a weighted confidence level associated with each event; and including the weighted confidence levels in a histogram. According to embodiments, the feature extractor 212 may be, include, be similar to, or be included in, aspects of embodiments of the histogram generator described in U.S. Application No. 62/486,926, filed on Apr. 18, 2017, entitled "ANNOTATION WAVEFORM;" U.S. Application No. 62/486,909, filed on Apr. 18, 2017, entitled "ELECTROANATOMICAL MAPPING TOOLS FACILITATED BY ACTIVATION WAVEFORMS;" and/or U.S. Application No. 62/486,920, filed on Apr. 18, 2017, entitled "ANNOTATION HISTOGRAM;" incorporated above.

As shown in FIG. 2, the processing unit 200 includes a region of interest (ROI) component 214. According to embodiments, the ROI component 214 is configured to determine a set of interesting cardiac signal features. According to embodiments, an "interesting" cardiac signal feature is a cardiac signal feature that has been designated as such, such as, for example, via user input, an automatic algorithm, and/or the like. In embodiments, for example, in embodiments, a user (e.g., a clinician) interacts with a graphical user interface (GUI) via a user input device to select a set of interesting cardiac signal features. In embodiments, the GUI may facilitate selection of one or more cardiac signal features, cardiac signal feature ranges, and/or the like, via interaction with a GUI. For example, in embodiments, a the GUI may include interactive representations of sliders, buttons, knobs, and/or the like, that enable user selection of various electrical signal features, device parameters, physiological parameters, environmental parameters, and/or the like. In embodiments, the GUI may allow the user to interact with the cardiac map directly (e.g., by utilizing a cursor to select points and/or regions of the map, hover over points and/or regions of the map, etc.) to facilitate identification of a set of interesting electrical signal features (and, thus, a region of interest). The processing unit 200 may be configured to determine a set of interesting electrical signal features based on the user interaction with the GUI.

In embodiments, the processing unit 200 may be configured to automatically determine a set of interesting electrical signal features such as, for example, by classifying electrical signal features as interesting based on one or more classification criteria. In embodiments, the classification criteria may be user selectable and/or adjustable. In embodiments, the criteria may be automatically selected and/or adjusted by the processing unit 200 in response to an indirectly related user input (e.g., a user input that facilitates display and/or adjustment of corresponding annotations. In embodiments, the set of interesting electrical signal features may be determined programmatically, to facilitate any number of different types of map functionality.

According to embodiments, the ROI component 214 may be configured to determine, based on the set of interesting cardiac signal features, an ROI. In embodiments, for example, the ROI includes the set of interesting cardiac signal features and/or the mapped information corresponding thereto. In embodiments, for example, the ROI component 214 may be configured to determine, for each cardiac signal feature of the set of cardiac signal features, a radius of influence. A radius of influence of an electrical signal feature is a metric (e.g., a scalar value, a vector, a combination of scalar values and/or vectors, etc.) that represents a spatial region within which the electrical signal feature has an effect and/or is likely to have an effect. For example, in embodiments, the radius of influence of a cardiac electrical signal feature may be a distance along the surface of the anatomical shell (e.g., a cardiac model) for which the cardiac signal feature has physiological significance—that is, for example, the radius of influence of a feature may correspond to a portion of the surface of the cardiac map that is annotated based at least in part on the feature.

In embodiments, the ROI component 214 may determine the radius of influence of an electrical signal feature in any number of ways such as, for example, to obtain (e.g. from a mapping engine) an indication of the portion of the cardiac map that was annotated at least partially based on the electrical signal feature. In embodiments, the ROI component 214 may determine the radius of influence of an electrical signal feature by determining a likelihood (e.g., probability) that the electrical signal feature (and/or other electrical signal features associated with the corresponding electrical signal) would have an influence (e.g., by contributing to a portion of operation of the heart, by contributing to an arrhythmia, by contributing to a signal measured within a certain distance, and/or the like. In embodiments, the radius of influence may refer to a surface distance (e.g., a cumulative distance along the contour of the surface of the map, rather than a Euclidean distance such as, e.g., the length of the radius of an imaginary sphere around the point) of a map.

According to embodiments, the ROI component 214 may be configured to determine the region of interest based on the determined radius of influence for each cardiac signal feature. That is, for example, the ROI component 214 may connect the map portions corresponding to the electrical signal features of the set of interesting electrical signal features to form the ROI. In embodiments, the ROI may be a continuous two-dimensional portion of the map, multiple disconnected two-dimensional portions of the map, and/or the like. In embodiments, an algorithm (e.g., aspects of embodiments of the methods described herein for vertex-based highlight generation, pixel-based highlight generation, etc.) may be configured to connect highlighted map portions (e.g., map portions corresponding to radii of influence) to form larger regions (e.g., ROIs, portions of ROIs, etc.). The algorithm may be configured to determine whether to connect the larger portions, which portions corresponding to radii of influence to connect, and/or the like. In embodiments, the ROI component 214 may be configured to perform interpolation such that, for example, two areas that are within some specified distance of one another may be connected (e.g., assuming one or more criteria are satisfied such as, e.g., there are no uninteresting points—data points that are to be left unhighlighted—between the two regions).

Additionally, the processing unit 200 includes a mapping engine 216 that is configured to facilitate presentation of a map 208 corresponding to a cardiac surface based on the electrical signals. In embodiments, the map 208 may include a voltage map, an activation map, a fractionation map, velocity map, confidence map, and/or the like. In embodiments, the mapping engine 216 may be, include, be similar to, be included within, and/or be otherwise integrated with the ROI component 214. In embodiments, the mapping engine 216 may be configured to facilitate display, via the display device, of the cardiac map and a representation of the region of interest. As shown, for example, a representation of a region of interest may include a first color saturation value that is different from a second color saturation value, where the second color saturation value is associated with at least one cardiac signal feature that is not included within the region of interest. In embodiments, more than one representation of a region of interest may be presented on the map.

Figure 3B:
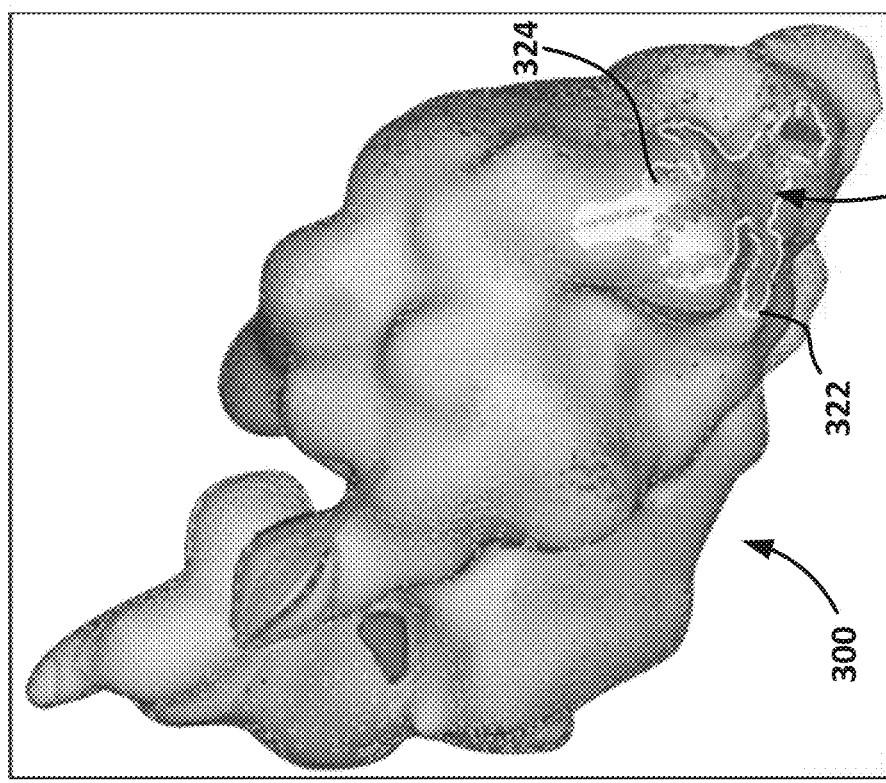
FIGS. 3A and 3B depict illustrative cardiac maps, in accordance with embodiments of the subject matter disclosed herein.

In embodiments, a representation of a region of interest is presented as a highlighted area of a map. Mesh pixels (pixels associated with a mesh that is used to generate the map) within the highlighted regions may appear to have a lighting effect that distinguishes them from the mesh pixels that are not within the highlighted regions, while preserving all of the information presented on the map (e.g., the annotation colors, hues, brightness, and other attributes associated with a region of interest are preserved when the region is highlighted because only the relative saturation level is adjusted—e.g., as opposed to dimming the map, adjusting transparency, etc.). In embodiments, to present the representation of a region of interest, portions of the map that are not within the region of interest may be de-saturated (e.g., displayed with a lower saturation value than the saturation value with which those areas were displayed prior to presenting the representation), while portions of the map within the region of interest may be oversaturated or at least displayed with a saturation value that exceeds the saturation value with which the regions were displayed prior to presenting the representation of the region of interest. In embodiments, an amount of saturation of a highlighted area is greater than the amount of saturation of a non-highlighted area. According to embodiments, the saturation of highlighted areas and/or non-highlighted areas may be selected, controlled, and/or otherwise influenced (e.g., controlled within certain allowed parameters) by a user. An illustrative highlighting operation is depicted in FIGS. 3A & 3B.

Figure 3A:
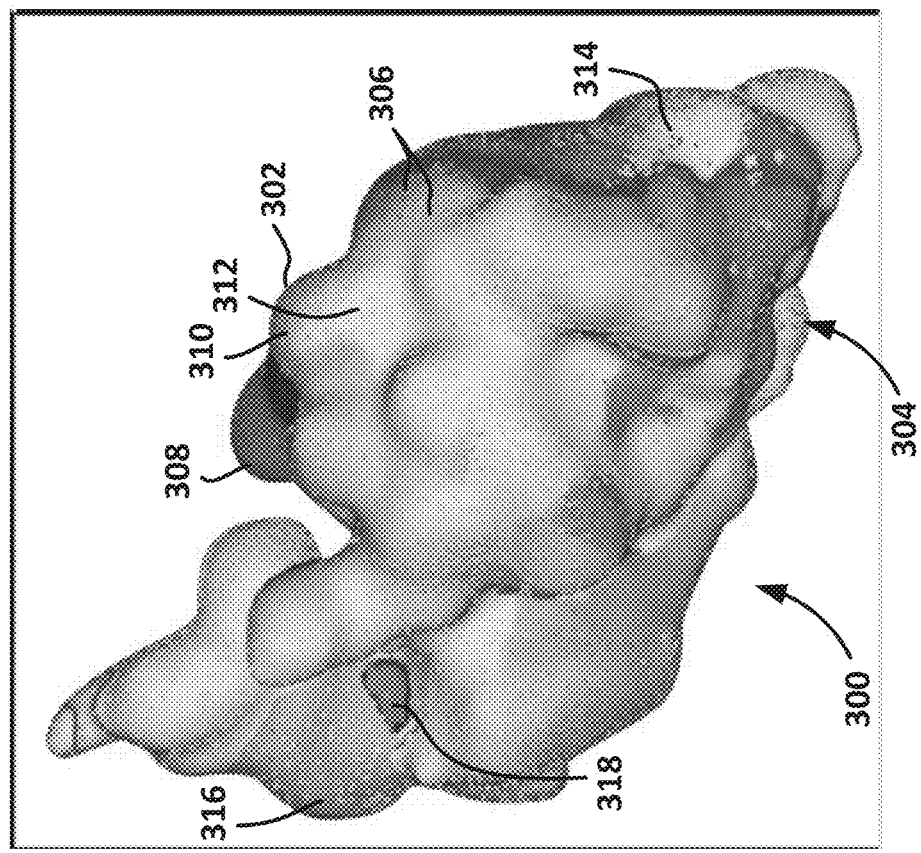

FIG. 3A depicts an illustrative screenshot from an interactive graphical user interface (GUI) presented using a display device associated with a cardiac mapping system, showing an illustrative cardiac map 300, in accordance with embodiments of the subject matter disclosed herein. According to embodiments, the cardiac mapping system may be, be similar to, include similar features as, include, or be included within the mapping system 100 depicted in FIG. 1. In embodiments, the GUI may be configured to present only one view of the cardiac map 300 at a time. In embodiments, the GUI may be configured to present, simultaneously, sequentially, and/or alternatively, any number of different views of any number of cardiac maps. In embodiments, for example, the GUI may be configured to present a first cardiac map having annotations representing activations and a second cardiac map having annotations representing electrical potential, current density, and/or the like.

As shown in FIG. 3A, the cardiac map 300 includes an anatomical shell 302 and annotations 304 displayed on the anatomical shell 302. In embodiments, the map may be an activation map, on which activation locations are indicated by raised bumps 306. In embodiments, raised bumps 306 (or other displayed features) may be used to indicate any number of different metrics, values, events, and/or the like. In embodiments, annotations (e.g., electrical signal features, quantities corresponding to—e.g., derived from—electrical signal features) may be represented using colors 308, 310, 312, 314, 316, and 318. Although six distinct colors are discussed herein, any number of colors may be used for such representations. In embodiments, in addition to, or in lieu of, colors, other representations may be used to represent activations such as, for example, textures, location markers, curves, vectors, and/or the like. In embodiments, the raised bumps 306 may be configured to represent a location associated with an acquired electrical signal (e.g., an EGM), a virtual location associated with an aggregation of acquired electrical signals, and/or the like. In embodiments, the GUI may also include a legend (not shown) configured to indicate the values represented by the annotation colors 308, 310, 312, 314, 316, and 318.

Embodiments facilitate presenting, on a cardiac map, a representation of a region of interest (ROI) by highlighting a corresponding portion of the cardiac map. FIG. 3B an illustrative screenshot from an interactive GUI, showing another view of the cardiac map 300 depicted in FIG. 3A, in accordance with embodiments of the subject matter disclosed herein. According to embodiments, the cardiac map 300 may be, or include, one or more selectable GUI elements such that, for example, a user can move a cursor over a portion of the cardiac map 300 and select the portion of the cardiac map 300 to which the cursor points, for example, by pressing a mouse button, tapping a touchscreen, and/or the like.

According to embodiments, for example, the GUI may be configured to receive, from a user input device, a selection of a region of the cardiac map 300. The user input device used to make the selection may include a mouse, a touchscreen and/or the like, that is used to manipulate a selection tool that is provided on the GUI provided by the display device. The selection tool may include, for example, a brush, a cursor for enclosing the selected region by drawing a freeform shape around the region, an expandable polygon selection tool, a virtual probe, and/or the like, and may be, in embodiments, selected from a number of optional selection tools. In embodiments, the selection tool may have an adjustable size, behavior and/or other characteristics thereof. In this manner, for example, a user may select a desired selection tool and a size thereof. Selecting a region of the map 300 may include, for example, circling the region of the map using a mouse or touchscreen device to manipulate a cursor, brushing over the region of the map using an input device to manipulate a brush, and/or the like. According to embodiments, one or more portions of a map may be interactive such that a user may position a mouse cursor over a portion of the map, and interact with that portion (e.g., by clicking a right mouse button) to reveal additional information and/or functionality.

In embodiments, in response to receiving an indication of the user selection of a portion of the cardiac map 300, the processing unit may cause a corresponding region (referred to herein as the "selected region") of the map 300 to be highlighted. Similarly, the GUI may include one or more selectable elements separate from the cardiac map 300 (e.g., selectable waveforms, histograms, EGMs, parameters, etc.) that may be selected using a user input device to cause the processing unit to highlight a corresponding portion 320 of the map 300. In embodiments, information corresponding to the user selection may be, include, or be included in a region of interest (ROI), and the highlighted portion 320 of the map 300 may be, include, or be included in a representation of the ROI.

According to embodiments, for example, a user may interact with a mouse, and may manipulate the mouse to move a mouse cursor over a portion of the map. When the user presses and holds a mouse button, the processing unit may determine a ray extending from the location of the point of the mouse cursor to the mesh, e.g., in a direction that is normal to the mesh (or in a direction associated with movement of the mouse cursor, etc.). The processing unit may be configured to determine a location (e.g., a mesh element) at which the ray intersects the mesh, and may be configured to determine one or more pixels associated with the mesh element. The one or more pixels may be highlighted as a representation of a region of interest (ROI). In embodiments, the user may expand the region of interest by moving the mouse cursor, while holding down the mouse button, causing the process to additively generate a larger ROI.

The representation 320 of the ROI may be configured to emphasize the portion of the map 300 corresponding to the ROI. In embodiments, for example, the representation 320 of ROI may be distinguished from adjacent regions of the map 300 by being highlighted. That is, for example, the representation 320 of the ROI may be a highlighting of the corresponding portion of the map (e.g., by presenting the representations of the electrical signal features in the representation 320 using a color saturation different than the color saturation of other portions of the map 300). In embodiments, as shown in FIG. 3B, the representation 320 of the ROI may include a border 322 outlining the region. The border 322 may presented in a color that is different than one or more of the colors used to annotate the map 300 (e.g., a color different than any color used in any pixel or group of pixels of a certain size disposed adjacent the border). For example, in embodiments, the border 322 may be white. The border 322 may be configured to help delineate the representation 320 of the ROI, create the feel of a discrete region, and/or assist in situations where some display devices and/or lighting conditions make the highlighting itself more difficult for a user to see. In embodiments, individual electrical signal features and/or locations may be indicated using representations 324 such as "Xs," raised bumps, and/or the like.

The illustrative processing unit 200 shown in FIG. 2 and the illustrative cardiac maps 300 are not intended to suggest any limitation as to the scope of use or functionality of embodiments of the present disclosure. Neither should the illustrative processing unit 200 and/or the cardiac map 500 be interpreted as having any dependency or requirement related to any single component or combination of components illustrated therein. Additionally, any one or more of the components and/or features depicted in FIGS. 2, 3A, and 3B may be, in embodiments, integrated with various ones of the other components and/or features depicted therein (and/or components not illustrated), all of which are considered to be within the ambit of the subject matter disclosed herein. For example, the acceptor 210 may be integrated with the feature extractor 212, the ROI component 214, and/or the mapping engine 216. In embodiments, the processing unit 200 may not include an acceptor 210, while in other embodiments, the acceptor 210 may be configured to receive electrical signals from a memory device, a communication component, and/or the like.

Additionally, the processing unit 200 may (alone and/or in combination with other components of the system 100 depicted in FIG. 1, and/or other components not illustrated) perform any number of different functions and/or processes associated with cardiac mapping (e.g., triggering, blanking, field mapping, etc.) such as, for example, those described in U.S. Pat. No. 8,428,700, entitled "ELECTROANATOMICAL MAPPING;" U.S. Pat. No. 8,948,837, entitled "ELECTROANATOMICAL MAPPING;" U.S. Pat. No. 8,615,287, entitled "CATHETER TRACKING AND ENDOCARDIUM REPRESENTATION GENERATION;" U.S. Patent Publication 2015/0065836, entitled "ESTIMATING THE PREVALENCE OF ACTIVATION PATTERNS IN DATA SEGMENTS DURING ELECTROPHYSIOLOGY MAPPING;" U.S. Pat. No. 6,070,094, entitled "SYSTEMS AND METHODS FOR GUIDING MOVABLE ELECTRODE ELEMENTS WITHIN MULTIPLE-ELECTRODE STRUCTURE;" U.S. Pat. No. 6,233,491, entitled "CARDIAC MAPPING AND ABLATION SYSTEMS;" U.S. Pat. No. 6,735,465, entitled "SYSTEMS AND PROCESSES FOR REFINING A REGISTERED MAP OF A BODY CAVITY;" the disclosures of which are hereby expressly incorporated herein by reference.

According to embodiments, various components of the mapping system 100, illustrated in FIG. 1, and/or the processing unit 200, illustrated in FIG. 2, may be implemented on one or more computing devices. A computing device may include any type of computing device suitable for implementing embodiments of the disclosure. Examples of computing devices include specialized computing devices or general-purpose computing devices such "workstations," "servers," "laptops," "desktops," "tablet computers," "handheld devices," "general-purpose graphics processing units (GPGPUs)," and the like, all of which are contemplated within the scope of FIGS. 1 and 2 with reference to various components of the system 100 and/or processing unit 200.

In embodiments, a computing device includes a bus that, directly and/or indirectly, couples the following devices: a processor, a memory, an input/output (I/O) port, an I/O component, and a power supply. Any number of additional components, different components, and/or combinations of components may also be included in the computing device. The bus represents what may be one or more busses (such as, for example, an address bus, data bus, or combination thereof). Similarly, in embodiments, the computing device may include a number of processors, a number of memory components, a number of I/O ports, a number of I/O components, and/or a number of power supplies. Additionally any number of these components, or combinations thereof, may be distributed and/or duplicated across a number of computing devices.

In embodiments, memory (e.g., the storage device 160 depicted in FIG. 1, and/or the memory 204 depicted in FIG. 2) includes computer-readable media in the form of volatile and/or nonvolatile memory and may be removable, nonremovable, or a combination thereof. Media examples include Random Access Memory (RAM); Read Only Memory (ROM); Electronically Erasable Programmable Read Only Memory (EEPROM); flash memory; optical or holographic media; magnetic cassettes, magnetic tape, magnetic disk storage or other magnetic storage devices; data transmissions; and/or any other medium that can be used to store information and can be accessed by a computing device such as, for example, quantum state memory, and/or the like. In embodiments, the memory 160 and/or 204 stores computer-executable instructions for causing a processor (e.g., the processing unit 120 depicted in FIG. 1 and/or the processor 202 depicted in FIG. 2) to implement aspects of embodiments of system components discussed herein and/or to perform aspects of embodiments of methods and procedures discussed herein.

Computer-executable instructions may include, for example, computer code, machine-useable instructions, and the like such as, for example, program components capable of being executed by one or more processors associated with a computing device. Examples of such program components include the electrical signal feature 206, the map 208, the acceptor 210, the feature extractor 212, the ROI component 214, and/or the mapping engine 216. Program components may be programmed using any number of different programming environments, including various languages, development kits, frameworks, and/or the like. Some or all of the functionality contemplated herein may also, or alternatively, be implemented in hardware and/or firmware.

Figure 4:
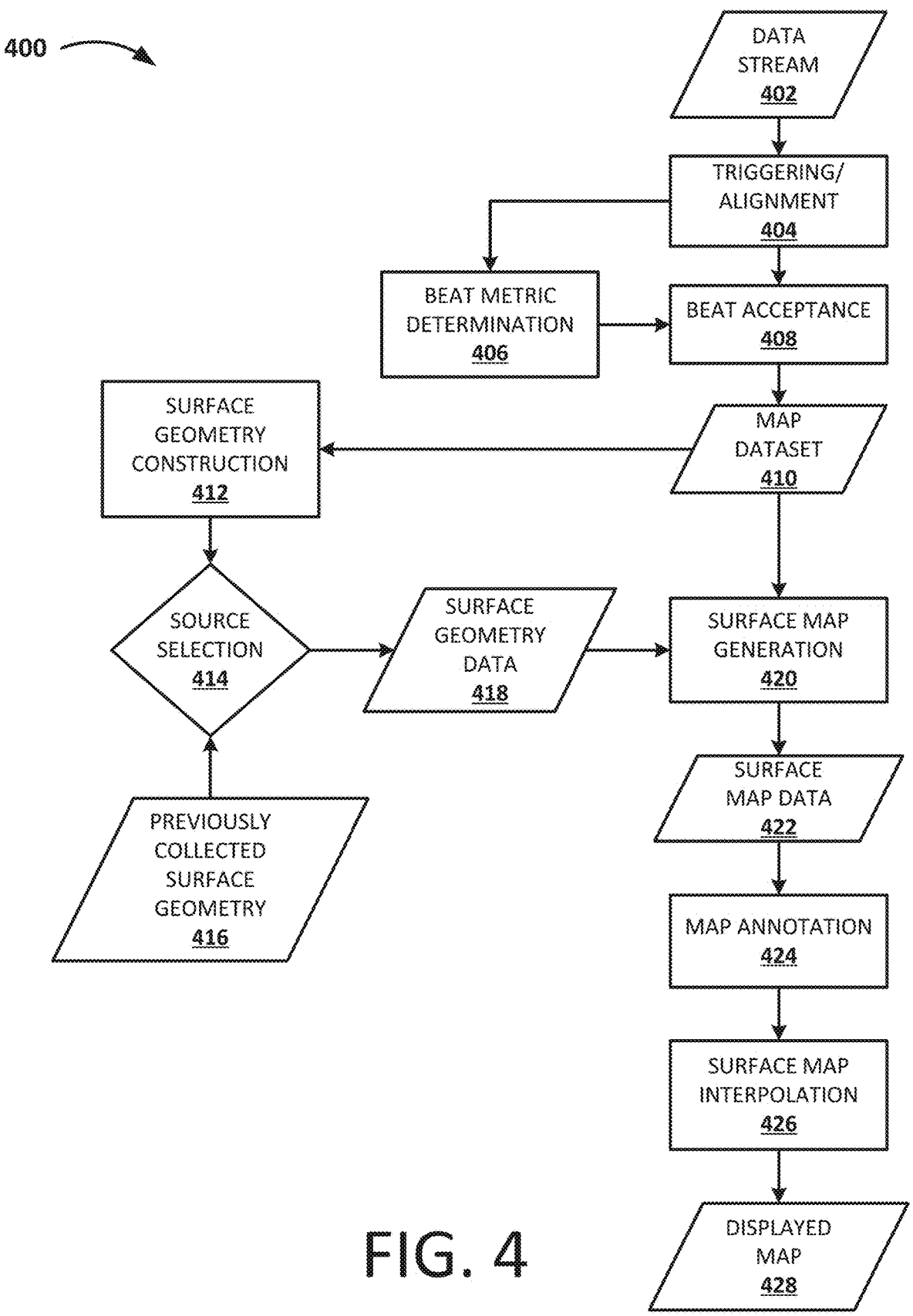
FIG. 4 is a flow diagram depicting an illustrative process for generating a cardiac map, in accordance with embodiments of the subject matter disclosed herein.

FIG. 4 is a flow diagram of an illustrative process 400 for automated electro-anatomical mapping, in accordance with embodiments of the disclosure. Aspects of embodiments of the method 400 may be performed, for example, by a processing unit (e.g., the processing unit 120 depicted in FIG. 1, and/or the processing unit 200 depicted in FIG. 2). A data stream 402 containing multiple signals is first input into the system (e.g., the cardiac mapping system 100 depicted in FIG. 1). During the automated electro-anatomical mapping process, a data stream 402 provides a collection of physiological and non-physiological signals that serve as inputs to the mapping process. The signals may be collected directly by the mapping system, and/or obtained from another system using an analog or digital interface. The data stream 402 may include signals such as unipolar and/or bipolar intracardiac electrograms (EGMs), surface electrocardiograms (ECGs), electrode location information originating from one or more of a variety of methodologies (magnetic, impedance, ultrasound, real time MRI, etc.), tissue proximity information, catheter force and/or contact information obtained from one or more of a variety of methodologies (force spring sensing, piezo-electric sensing, optical sensing etc.), catheter tip and/or tissue temperature, acoustic information, catheter electrical coupling information, catheter deployment shape information, electrode properties, respiration phase, blood pressure, other physiological information, and/or the like.

For the generation of specific types of maps, one or more signals may be used as one or more references, during a triggering/alignment process 404, to trigger and align the data stream 402 relative to the cardiac, other biological cycle and/or an asynchronous system clock resulting in beat datasets. Additionally, for each incoming beat dataset, a number of beat metrics are computed during a beat metric determination process 406. Beat metrics may be computed using information from a single signal, spanning multiple signals within the same beat and/or from signals spanning multiple beats. The beat metrics provide multiple types of information on the quality of the specific beat dataset and/or likelihood that the beat data is good for inclusion in the map dataset. A beat acceptance process 408 aggregates the criteria and determines which beat datasets will make up the map dataset 410. The map dataset 410 may be stored in association with a 3D grid that is dynamically generated during data acquisition.

Surface geometry data may be generated concurrently during the same data acquisition process using identical and/or different triggering and/or beat acceptance metrics employing a surface geometry construction process 412. This process constructs surface geometry using data such as electrode locations and catheter shape contained in the data stream. Additionally, or alternatively, previously collected surface geometry 416 may be used as an input to surface geometry data 418. Such geometry may have been collected previously in the same procedure using a different map dataset, and/or using a different modality such as CT, MRI, ultrasound, rotational angiography, and/or the like, and registered to the catheter locating system. The system performs a source selection process 414, in which it selects the source of the surface geometry data and provides surface geometry data 418 to a surface map generation process 420. The surface map generation process 420 is employed to generate surface map data 422 from the map dataset 410 and surface geometry data 418.

The surface geometry construction algorithm generates the anatomical surface on which the electroanatomical map is displayed. Surface geometry can be constructed, for example, using aspects of a system as described U.S. patent application Ser. No. 12/437,794, entitled "Impedance Based Anatomy Generation" and filed on May 8, 2008; and/or U.S. Pat. No. 8,948,837, entitled "Electroanatomical Mapping" and issued on Feb. 3, 2015, the contents of each of which is incorporated by reference herein in its entirety. Additionally, or alternatively, an anatomical shell can be constructed by the processing unit by fitting a surface on electrode locations that are determined either by the user or automatically to be on the surface of the chamber. In addition, a surface can be fit on the outermost electrode and/or catheter locations within the chamber.

As described, the map dataset 410 from which the surface is constructed can employ identical or different beat acceptance criteria from those used for electrical and other types of maps. The map dataset 410 for surface geometry construction can be collected concurrently with electrical data or separately. Surface geometry can be represented as a mesh containing a collection of vertices (points) and the connectivity between them (e.g. triangles). Alternatively, surface geometry can be represented by different functions such as higher order meshes, non-uniform rational basis splines (NURBS), and/or curvilinear shapes.

The generation process 420 generates surface map data 422. The surface map data 422 may provide information on cardiac electrical excitation, cardiac motion, tissue proximity information, tissue impedance information, force information, and/or any other collected information desirable to the clinician. The combination of map dataset 410 and surface geometry data 418 allows for surface map generation. The surface map is a collection of values or waveforms (e.g., EGMs) on the surface of the chamber of interest, whereas the map dataset can contain data that is not on the cardiac surface. One approach for processing the map dataset 410 and surface geometry data 418 to obtain a surface map dataset 422 is described in U.S. Pat. No. 7,515,954, entitled "NON-CONTACT CARDIAC MAPPING, INCLUDING MOVING CATHETER AND MULTI-BEAT INTEGRATION" and filed Jun. 13, 2006, the contents of which is incorporated by reference herein in its entirety.

Alternatively, or in combination with the method above, an algorithm that applies acceptance criteria to individual electrodes can be employed. For example, electrode locations exceeding a set distance (e.g., 3 mm) from surface geometry can be rejected. Another algorithm can incorporate tissue proximity information using impedance for inclusion in the surface map data. In this case only electrode location whose proximity value is less than 3 mm might be included. Additional metrics of the underlying data can also be used for this purpose. For example, EGM properties similar to beat metrics can be assessed on a per electrode basis. In this case metrics such as far field overlap and/or EGM consistency can be used. It should be understood that variations on the method to project points from the map dataset 410 to the surface and/or to select appropriate points can exist.

Once obtained, the surface map data 422 may be further processed to annotate desired features from the underlying data, a process defined as surface map annotation 424. Once data is collected into surface map data 422, attributes relating to the collected data may be automatically presented to the user. These attributes can be automatically determined and applied to the data by the computer system and are referred to herein as annotations. Exemplary annotations include activation time, the presence of double activation or fractionation, voltage amplitude, spectral content, and/or the like. Due to the abundance of data available in automated mapping (e.g., mapping completed by the computer system with minimal human input related to the incoming data), it is not practical for the operator to review and annotate data manually. However, human input can be a valuable addition to the data, and so when user input is provided it is necessary for the computer system to automatically propagate and apply it to more than one data point at a time.

It may be possible to use the computer system to automatically annotate activation time, voltage, and other characteristics of individual EGMs. Activation time detection may use methods similar to those previously described to detect a trigger and can similarly benefit from the use of blanking and powered triggering operator. Desired annotations may include instantaneous potential, activation time, voltage amplitude, dominant frequency and/or other properties of the signal. Once computed, the annotations may be displayed superimposed on chamber geometry. In embodiments, a gap-filling surface map interpolation may be employed 426. For example, in embodiments, a gap-filling interpolation may be employed where a distance between a point on the surface to a measured EGM exceeds a threshold, as this may indicate, for example, that grid-based interpolation, as described herein, may not be as effective in that situation. Displayed maps 428 can be computed and displayed separately, and/or overlaid on top of each other.

The illustrative method 400 shown in FIG. 4 is not intended to suggest any limitation as to the scope of use or functionality of embodiments of the present disclosure. Neither should the illustrative method 400 be interpreted as having any dependency nor requirement related to any single aspect or combination of aspects illustrated therein. Additionally, any one or more of the aspects depicted in FIG. 4 may be, in embodiments, integrated with various ones of the other aspects depicted therein (and/or components not illustrated), all of which are considered to be within the ambit of the present disclosure.

Figure 5:
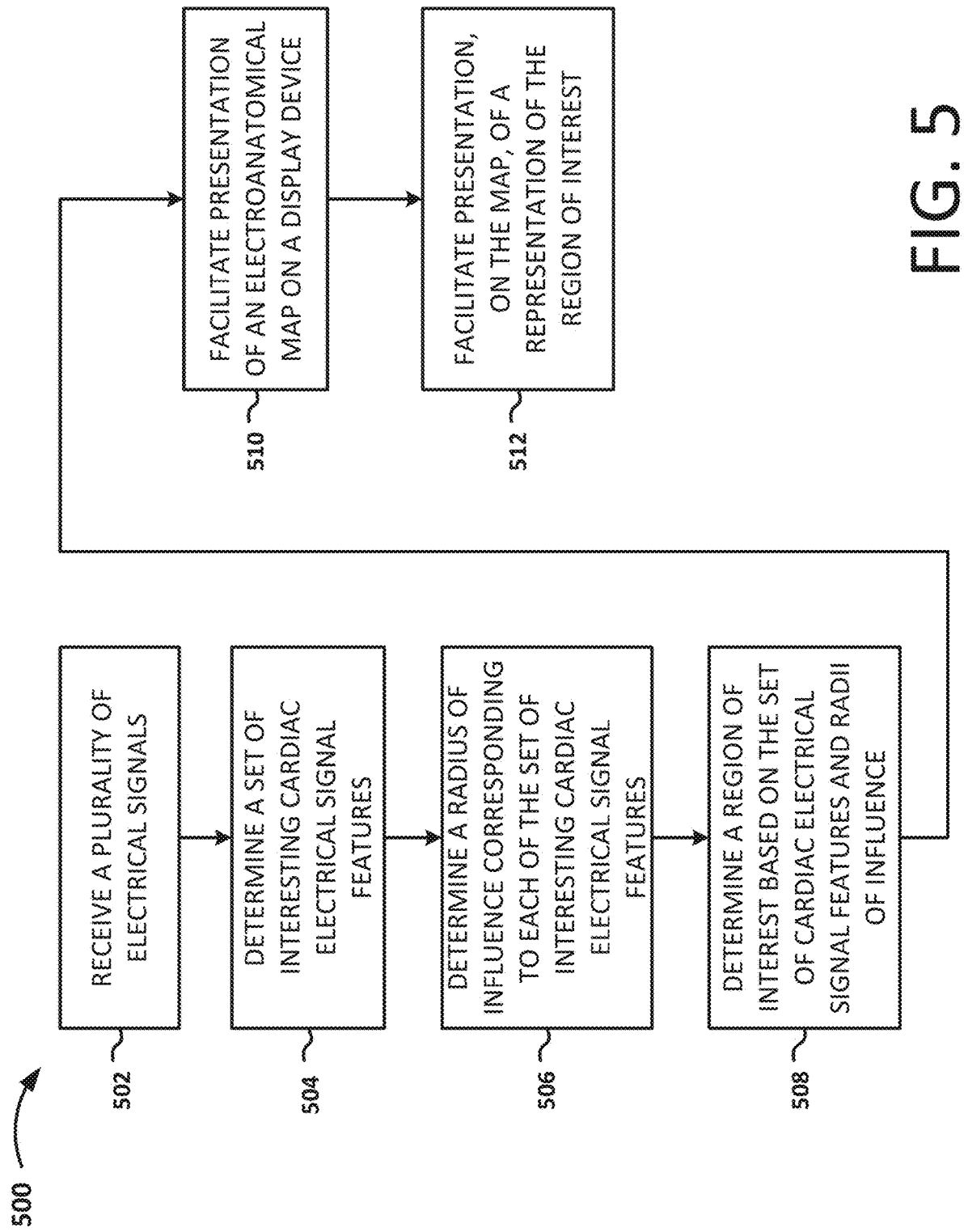
FIG. 5 is a flow diagram depicting an illustrative method of processing electrophysiological information, in accordance with embodiments of the subject matter disclosed herein.

FIG. 5 is a flow diagram depicting an illustrative method 500 of processing electrophysiological information, in accordance with embodiments of the disclosure. Aspects of embodiments of the method 500 may be performed, for example, by a processing unit (e.g., the processing unit 120 depicted in FIG. 1, and/or the processing unit 200 depicted in FIG. 2). Embodiments of the method 500 include receiving a plurality of electrical signals (block 402). The electrical signals may be received from a catheter, a memory device, a computing device, and/or the like. The catheter may be any catheter having one or more electrodes configured to obtain electrical signals (e.g., the mapping catheter 110 depicted in FIG. 1, a CS catheter, an ablation catheter, etc.). The processing unit also may receive an indication of a measurement location corresponding to each of the electrical signals. As explained above, with respect to FIG. 4, the processing unit and/or other components (e.g., the electrical module 140 depicted in FIG. 1) may be configured to determine whether to accept particular electrical signals (e.g., beats) based on one or more beat acceptance criteria.

According to embodiments, cardiac electric signal features may be extracted from the cardiac electrical signals (e.g., EGMs). Examples of features of the cardiac electrical signals include, but are not limited to, activation times, minimum voltage values, maximum voltages values, maximum negative time-derivatives of voltages, instantaneous potentials, voltage amplitudes, dominant frequencies, peak-to-peak voltages, and/or the like. Each of the respective points at which a cardiac electrical signal is sensed may have a corresponding set of three-dimensional position coordinates. For example, the position coordinates of the points may be represented in Cartesian coordinates. Other coordinate systems can be used, as well. In embodiments, an arbitrary origin is used and the respective position coordinates are defined with respect to the arbitrary origin. In some embodiments, the points have non-uniform spacing, while in other embodiments, the points have uniform spacing. In embodiments, the point corresponding to each sensed cardiac electrical signal may be located on the endocardial surface of the heart and/or below the endocardial surface of the heart.

As shown in FIG. 5, embodiments of the method 500 include determining a set of interesting cardiac electrical signal features (block 504). The set of interesting cardiac electrical signal features may be determined, e.g., via user input and/or an automatic algorithm. Embodiments of the method 500 include determining a radius of influence corresponding to each cardiac electrical signal feature of the set of interesting cardiac electrical signal features (block 506); and determining a region of interest (ROI) based on the set of interesting cardiac electrical signals and the corresponding radii of influence (block 508). Embodiments of the method 500 further include facilitating presentation of an electroanatomical map on a display device (block 510) and facilitating presentation, on the map, of a representation of the ROI (block 512).

In embodiments, a cardiac map may be generated and/or annotated based, at least in part, on the cardiac electrical signal features and/or the activation waveform (which may also be a cardiac electrical signal feature). In embodiments, the cardiac map may also be generated and/or annotated, at least in part, using any number of other signals, techniques, and/or the like. For example, embodiments may utilize impedance mapping techniques to generate and/or annotate one or more portions of the cardiac map such as, for example, an anatomical shell upon which electrical signal features are represented. In embodiments, a surface may be fitted on one or more of the points associated with the cardiac electrical signals to generate a shell representing the endocardial surface of the one or more cardiac structures. In embodiments, a surface may also be fitted on one or more of the points associated with the cardiac electrical signals to generate a shell representing an epicardium surface or other excitable cardiac tissue. In embodiments, one or more of the cardiac electrical signal features at the corresponding points can be included on the shell to generate a cardiac map of the one or more cardiac structures. For example, embodiments may include displaying annotations on the cardiac map that represent features, extracted from the cardiac electrical signals and/or derived from other features, such as, for example, activation times, minimum voltage values, maximum voltages values, maximum negative time-derivatives of voltages, instantaneous potentials, voltage amplitudes, dominant frequencies, peak-to-peak voltages, and/or the like.

Cardiac electrical signal features may be represented on the cardiac map and may be, or include, any features extracted from one or more corresponding sensed cardiac electrical signals and/or derived from one or more of such features. For example, a cardiac electrical signal feature may be represented by a color, such that if the cardiac electrical signal feature has an amplitude or other value within a first range then the cardiac electrical signal feature may be represented by a first color, whereas if the cardiac electrical signal feature has an amplitude or other value that is within a second range that is different than the first range, the cardiac electrical may be represented by a second color. As another example, the cardiac electrical signal feature may be represented by a number (e.g., a 0.2 mV sensed cardiac electrical signal feature can be represented by a 0.2 at its respective position on the surface map). Examples of a cardiac electrical signal feature that can be represented at the first surface point include, but are not limited to, an activation, an activation time, an activation duration, an activation waveform, a filtered activation waveform, an activation waveform characteristic, a filtered activation waveform characteristic, a minimum voltage value, a maximum voltages value, a maximum negative time-derivative of voltage, an instantaneous potential, a voltage amplitude, a dominant frequency, a peak-to-peak voltage, and/or the like.

In embodiments, other features such as, for example, non-electrical signal features, non-cardiac electrical signal features, and/or the like, can be represented on an anatomical map at respective locations. Examples of non-electrical signal features include, but are not limited to, features derived from magnetic resonance imaging, a computerized tomography scan, ultrasonic imaging, and/or the like.

According to embodiments, a GUI used for presenting the map may include any number of different input tools for manipulating the map. For example, the GUI may include a play/pause button, a tool configured to facilitate manual selection of the histogram bin or bins, tools configured to facilitate manual adjustment of parameters (e.g., signal baseline definitions, thresholds, EGM characteristics, filters, etc.), and/or the like. In embodiments, for example, the GUI may include a selection tool that can facilitate refining selections of highlighted EGMs, select particular EGMs and/or activations, and/or the like.

The illustrative method 500 shown in FIG. 5 is not intended to suggest any limitation as to the scope of use or functionality of embodiments of the present disclosure. Neither should the illustrative method 500 be interpreted as having any dependency nor requirement related to any single aspect or combination of aspects illustrated therein. Additionally, any one or more of the aspects depicted in FIG. 5 may be, in embodiments, integrated with various ones of the other aspects depicted therein (and/or components not illustrated), all of which are considered to be within the ambit of the present disclosure.

Figure 6:
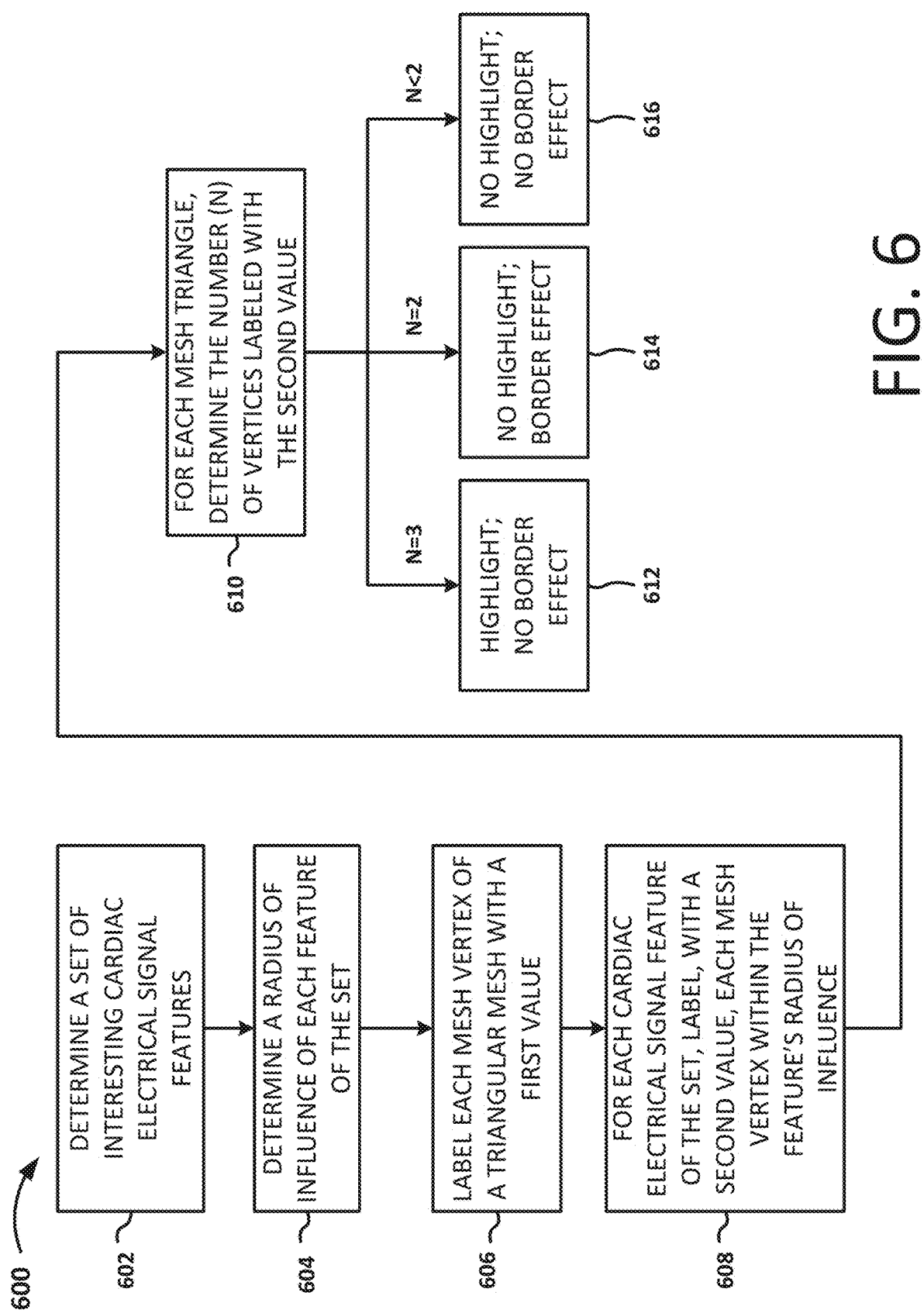
FIG. 6 is a flow diagram depicting an illustrative method of generating a representation of a region of interest, in accordance with embodiments of the subject matter disclosed herein.
Figure 7:
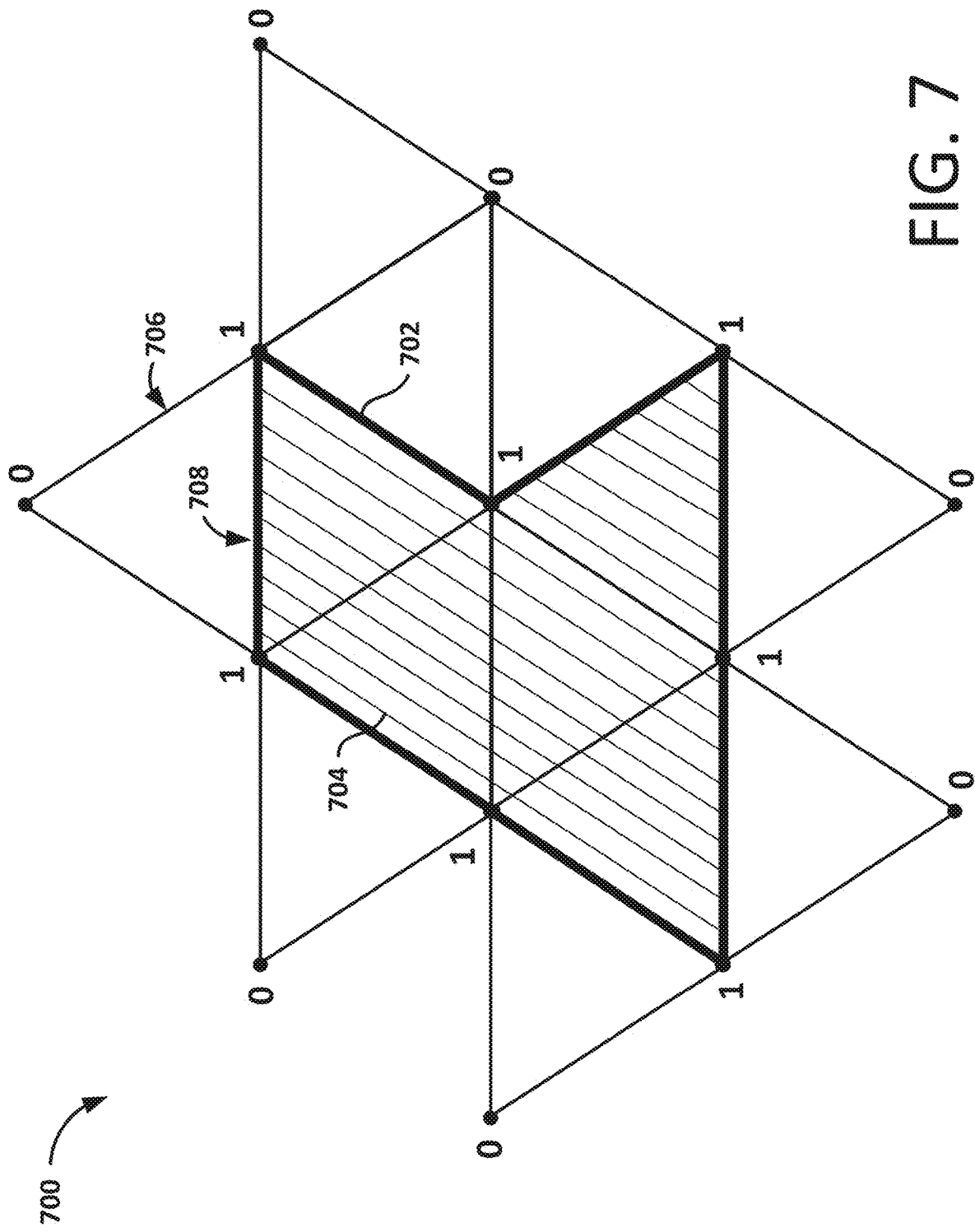
FIG. 7 is a conceptual schematic diagram depicting an illustrative example of generating a representation of a region of interest, using aspects of embodiments of the method depicted in FIG. 6, in accordance with embodiments of the subject matter disclosed herein.

FIG. 6 is a flow diagram depicting an illustrative method 600 of facilitating presentation of cardiac information, in accordance with embodiments of the subject matter disclosed herein. Aspects of embodiments of the method 600 may be performed, for example, by a processing unit (e.g., the processing unit 120 depicted in FIG. 1, and/or the processing unit 200 depicted in FIG. 2). FIG. 7 is a conceptual schematic diagram depicting an illustrative ROI highlighting operation, as described in embodiments of the method 600 depicted in FIG. 6, in accordance with embodiments of the subject matter disclosed herein. Embodiments of the method 600 include determining, from a plurality of cardiac electrical signal features extracted from a plurality of cardiac electrical signals, a set of interesting cardiac electrical signal features (block 602); and determining a radius of influence of each interesting cardiac electrical signal feature (block 604).

As shown in FIG. 6, embodiments of the method 600 further include labeling each mesh vertex of a mesh element of a mesh with a first value (block 606), and labeling (which may include, e.g., re-labeling) each mesh vertex of the mesh element of the mesh with a second value if a criterion is satisfied (block 608). In embodiments, the method 600 includes facilitating display of the representation of the region of interest based on the mesh vertex labels. That is, for example, in embodiments, as shown in FIG. 7, a triangular mesh 700 may be used for generating a cardiac map, and the first value may be 0, while the second value is 1. In embodiments, for example, all vertices of the mesh 700 may be initially labeled with a 0. For each cardiac electrical feature in the set of interesting cardiac electrical features, each vertex within the feature's radius of influence may be labeled with a 1. In embodiments, the subset of electrical signal features having radii of influence encompassing a vertex may be referred to as an influence subset. In embodiments, though some vertices may be labeled with a 1 multiple times (e.g., where the vertices fall within more than one radii of influence), those vertices may retain the label of 1.

Embodiments of the method 600 may further include determining the number of mesh vertices of the mesh element that are labeled with the second value (block 610), and apply presentation effects to the mesh based on the determined number. For example, as shown in FIG. 6, embodiments of the method 600 may include applying a highlighting effect, but no border effect, to a mesh element if the number of mesh vertices of the mesh element that are labeled with the second value is 3 (block 612). As shown in FIGS. 6 and 7, embodiments of the method 600 may include applying a border effect 702, but no highlighting effect 704, to the mesh element (e.g., 706) if the number of mesh vertices of the mesh element that are labeled with the second value is 2 (block 614); and applying no border effect 702 and no highlighting effect 704 to the mesh element if the number of mesh vertices of the mesh element that are labeled with the second value is less than 2 (block 616). The resulting representation 708 of the ROI may be bounded within the applied border effect, which may be presented, for example, as a border, as described herein (e.g., a white border).

The illustrative method 600 shown in FIG. 6 is not intended to suggest any limitation as to the scope of use or functionality of embodiments of the present disclosure. Neither should the illustrative method 600 be interpreted as having any dependency nor requirement related to any single aspect or combination of aspects illustrated therein. Additionally, any one or more of the aspects depicted in FIG. 6 may be, in embodiments, integrated with various ones of the other aspects depicted therein (and/or components not illustrated), all of which are considered to be within the ambit of the present disclosure.

Figure 8:
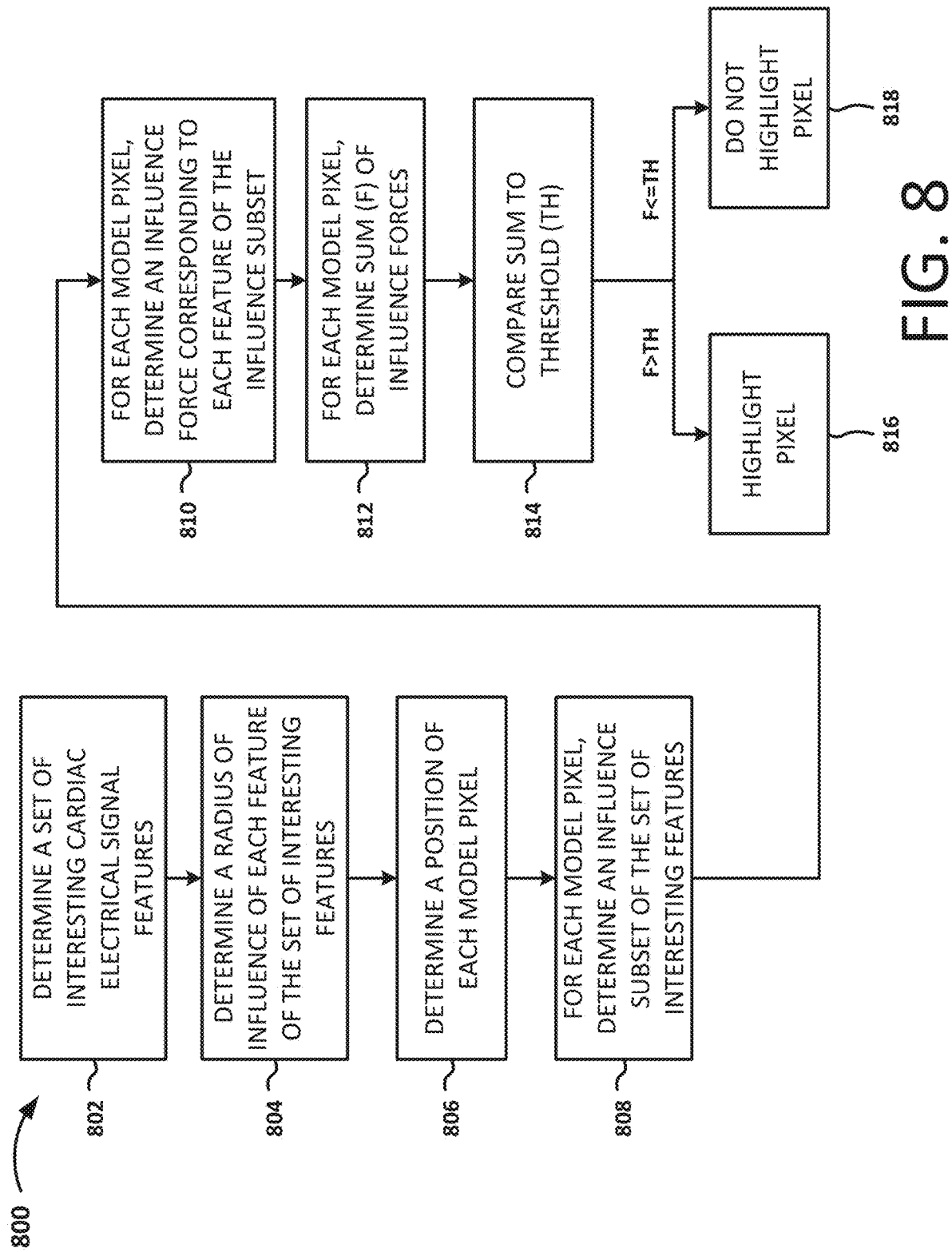
FIG. 8 is a flow diagram depicting an illustrative method of generating a representation of a region of interest, in accordance with embodiments of the subject matter disclosed herein.

Embodiments of the method 600 described above, with reference to FIGS. 6 and 7, may result in highlighted regions that have a more "jagged" appearance, due to the finite resolution of the triangles. In embodiments, a highlighted region with a more "smooth" appearance may be generated using embodiments of other methods such as, for example, a method loosely based on the concept of metaballs. FIG. 8 is a flow diagram depicting an illustrative method 800 of facilitating presentation of cardiac information, in accordance with embodiments of the subject matter disclosed herein. FIGS. 9 and 10A-C are conceptual schematic diagrams depicting aspects of an illustrative ROI highlighting operation, as described in embodiments of the method 800 depicted in FIG. 8, in accordance with embodiments of the subject matter disclosed herein. Aspects of embodiments of the method 800 may be performed, for example, by a processing unit (e.g., the processing unit 120 depicted in FIG. 1, and/or the processing unit 200 depicted in FIG. 2).

Embodiments of the method 800 include determining, from a plurality of cardiac electrical signal features extracted from a plurality of cardiac electrical signals, a set of interesting cardiac electrical signal features (block 802). Embodiments of the method 800 further include determining a radius of influence of each interesting cardiac electrical signal feature (block 804). As shown, embodiments of the method 800 include determining a position (e.g., P, depicted in FIG. 9) of each model pixel (block 806) and determining, for each model pixel, an influence subset of the set of interesting cardiac electrical signal features (block 808). An influence subset of the set of interesting cardiac electrical signal features may include, for example, each interesting cardiac electrical signal feature having a radius of influence that encompasses or otherwise affects a given pixel. In embodiments, for example, each electrical signal feature in the influence subset may be denoted as $e_i$, wherein i= 1, . . . , N.

Embodiments of the method 800 further include determining, for each model pixel, an influence force, $f_i$, associated with each cardiac electrical signal feature of the influence subset (block 810). In embodiments, for example, the influence force, $f_i$, may be a function of the electrical signal feature's position and P: $f_i = g(e_i, P)$, where g is some function that is dependent upon a surface distance, surf_dist, between $e_i$ and P. For example, in embodiments, $g = 1/\text{surf\_dist}(e_i, P)$. Surface distance may be determined (e.g., approximated) using any number of different techniques. In embodiments, as depicted for example, in FIG. 9, surface distance may be approximated by, based on normals 900, 902, and 904 to the mesh 906 corresponding to the positions associated with the features, $e_i$, and P, drawing an arc 908 such that the slope of the arc 908 at the two endpoints is perpendicular to the respective normals 900 and 902. The length of the arc 980 may be used as an approximation of the surface distance. In embodiments, this approximation of surface distance may be configured to be more accurate by using small radii of influence such that the curvature between the two endpoints is reduced.

According to embodiments, the method 800 may include determining, for each model pixel, a sum, F, of the influence forces (block 812): $F = \text{sum}(f(e_i, P))$ for each i. The method 800 may include comparing, for each model pixel, the sum, F, of the influence forces to a threshold, TH (block 814); and applying a highlighting effect to each model pixel if the sum, F, of the influence forces exceeds the threshold, TH (block 816) (F>TH); and not applying a highlighting effect if the sum, F, does not exceed the threshold, TH (block 818) (F<=TH).

In embodiments, the method 800 may include creating a border (not shown in FIG. 8, but conceptualized in FIGS. 10A-C). A border may be created using any number of different techniques. According to embodiments, for example, the border may be created by generating a shape 1000, using the highlighted pixels 1010, where the shape 1000 is expanded in size (e.g., by scaling, by a small factor, each highlighted pixel along the mesh's curvature). The shape may be rendered behind the highlighted pixels 1010 (e.g., as a layered effect, beneath the highlighted pixels), thereby resulting in a border 1020. In embodiments, although the shape 1010 and resulting border 1020 are depicted, in FIGS. 10B-C, for purposes of clarity of description, as being colored black, the shape 1010 and resulting border 1020 may be rendered in any number of different colors such as, for example, in white.

The illustrative method 800 shown in FIG. 8 is not intended to suggest any limitation as to the scope of use or functionality of embodiments of the present disclosure. Neither should the illustrative method 800 be interpreted as having any dependency nor requirement related to any single aspect or combination of aspects illustrated therein. Additionally, any one or more of the aspects depicted in FIG. 8 may be, in embodiments, integrated with various ones of the other aspects depicted therein (and/or components not illustrated), all of which are considered to be within the ambit of the present disclosure.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

We claim:

1. A method of presenting cardiac information, the method comprising:
   receiving a plurality of electrical signals;
   receiving an indication of a measurement location corresponding to each electrical signal of the plurality of electrical signals;
   generating, based on the plurality of electrical signals, the cardiac map, the cardiac map comprising a plurality of annotations representing a plurality of cardiac signal features;
   determining, from the plurality of cardiac signal features, a set of interesting cardiac signal features;

determining, based on the set of interesting cardiac signal features, a region of interest; and facilitating display, via the display device, of the cardiac map and a representation of the region of interest, the representation of the region of interest comprising a first color saturation value that is different from a second color saturation value, wherein the second color saturation value is associated with at least one cardiac signal feature that is not included within the region of interest.

2. The method of claim 1, further comprising:
determining, for each cardiac signal feature of the set of cardiac signal features, a radius of influence; and
determining the region of interest based on the determined radius of influence for each cardiac signal feature.

3. The method of either of claim 1 or 2, further comprising generating the cardiac map based on a mesh, and wherein the method further comprises:
labeling each mesh vertex of a mesh element of the mesh with a first value;
labeling each mesh vertex of the mesh element of the mesh with second value if a criterion is satisfied; and
facilitating display of the representation of the region of interest based on the mesh vertex labels.

4. The method of claim 2, further comprising:
determining a position of each model pixel;
determining, for each model pixel, an influence subset of the set of interesting cardiac electrical signal features;
determining, for each model pixel, an influence force associated with each cardiac electrical signal feature of the influence subset;
determining, for each model pixel, a sum of the influence forces;
comparing, for each model pixel, the sum of the influence forces to a threshold; and
applying a highlighting effect to each model pixel if the sum of the influence forces exceeds the threshold.

5. The method of claim 1, the cardiac electrical signal feature comprising at least one of an activation time, a detected activation, a minimum voltage value, a maximum voltages value, a maximum negative time-derivative of voltage, an instantaneous potential, a voltage amplitude, a dominant frequency, and a peak-to-peak voltage.

6. A system for facilitating display of cardiac information, the system comprising:
a display device configured to present a cardiac map; and
a processing unit configured to:
receive a plurality of electrical signals;
receive an indication of a measurement location corresponding to each electrical signal of the plurality of electrical signals;
generate, based on the plurality of electrical signals, the cardiac map, the cardiac map comprising a plurality of annotations representing a plurality of cardiac signal features;
determine, from the plurality of cardiac signal features, a set of interesting cardiac signal features;
determine, based on the set of interesting cardiac signal features, a region of interest; and
facilitate display, via the display device, of the cardiac map and a representation of the region of interest, the representation of the region of interest comprising a first color saturation value that is different from a second color saturation value, wherein the second color saturation value is associated with at least one cardiac signal feature that is not included within the region of interest.

7. The system of claim 6, wherein the processing unit is further configured to:
determine, for each cardiac signal feature of the set of cardiac signal features, a radius of influence; and
determine the region of interest based on the determined radius of influence for each cardiac signal feature.

8. The system of claim 7, wherein the processing unit is configured to generate the cardiac map based on a mesh, and wherein the processing unit is further configured to:
label each mesh vertex of a mesh element of the mesh with a first value;
label each mesh vertex of the mesh element of the mesh with second value if a criterion is satisfied; and
facilitate display of the representation of the region of interest based on the mesh vertex labels.

9. The system of claim 8, wherein the mesh comprises a triangular mesh, wherein the first value comprises a 0, and wherein the second value comprises a 1, and wherein the processing unit is configured to:
determine the number of mesh vertices of the mesh element that are labeled with the second value;
apply a highlighting effect, but no border effect, to the mesh element if the number of mesh vertices of the mesh element that are labeled with the second value is 3;
apply a border effect, but no highlighting effect, to the mesh element if the number of mesh vertices of the mesh element that are labeled with the second value is 2; and
apply no border effect and no highlighting effect to the mesh element if the number of mesh vertices of the mesh element that are labeled with the second value is less than 2.

10. The system of claim 7, wherein the processing unit is further configured to:
determine a position of each model pixel;
determine, for each model pixel, an influence subset of the set of interesting cardiac electrical signal features;
determine, for each model pixel, an influence force associated with each cardiac electrical signal feature of the influence subset;
determine, for each model pixel, a sum of the influence forces;
compare, for each model pixel, the sum of the influence forces to a threshold; and
apply a highlighting effect to each model pixel if the sum of the influence forces exceeds the threshold.

11. The system of claim 10, the representation of the region of interest comprising a border, wherein the processing unit is further configured to:
generate a scaled region of interest shape corresponding to the region of interest; and
generate the border by facilitating display of the highlighted pixels above the scaled region of interest shape.

12. The system of claim 6, the cardiac electrical signal feature comprising at least one of an activation time, a detected activation, a minimum voltage value, a maximum voltages value, a maximum negative time-derivative of voltage, an instantaneous potential, a voltage amplitude, a dominant frequency, and a peak-to-peak voltage.

13. A method of presenting cardiac information, the method comprising:
receiving a plurality of electrical signals;
receiving an indication of a measurement location corresponding to each electrical signal of the plurality of electrical signals;

generating, based on the plurality of electrical signals, the cardiac map, the cardiac map comprising a plurality of annotations representing a plurality of cardiac signal features;

determining, from the plurality of cardiac signal features, a set of interesting cardiac signal features;

determining, based on the set of interesting cardiac signal features, a region of interest; and facilitating display, via the display device, of the cardiac map and a representation of the region of interest, the representation of the region of interest comprising a first color saturation value that is different from a second color saturation value, wherein the second color saturation value is associated with at least one cardiac signal feature that is not included within the region of interest.

14. The method of claim 13, further comprising:
determining, for each cardiac signal feature of the set of cardiac signal features, a radius of influence; and
determining the region of interest based on the determined radius of influence for each cardiac signal feature.

15. The method of claim 13, further comprising generating the cardiac map based on a mesh, and wherein the method further comprises:
labeling each mesh vertex of a mesh element of the mesh with a first value;
labeling each mesh vertex of the mesh element of the mesh with second value if a criterion is satisfied; and
facilitating display of the representation of the region of interest based on the mesh vertex labels.

16. The method of claim 15, wherein the mesh comprises a triangular mesh, wherein the first value comprises a 0, and wherein the second value comprises a 1, the method further comprising:
determining the number of mesh vertices of the mesh element that are labeled with the second value;
applying a highlighting effect, but no border effect, to the mesh element if the number of mesh vertices of the mesh element that are labeled with the second value is 3;
applying a border effect, but no highlighting effect, to the mesh element if the number of mesh vertices of the mesh element that are labeled with the second value is 2; and
applying no border effect and no highlighting effect to the mesh element if the number of mesh vertices of the mesh element that are labeled with the second value is less than 2.

17. The method of claim 13, further comprising:
determining a position of each model pixel;
determining, for each model pixel, an influence subset of the set of interesting cardiac electrical signal features;
determining, for each model pixel, an influence force associated with each cardiac electrical signal feature of the influence subset;
determining, for each model pixel, a sum of the influence forces;
comparing, for each model pixel, the sum of the influence forces to a threshold; and
applying a highlighting effect to each model pixel if the sum of the influence forces exceeds the threshold.

18. The method of claim 17, the representation of the region of interest comprising a border, wherein the processing unit is further configured to:
generate a scaled region of interest shape corresponding to the region of interest; and
generate the border by facilitating display of the highlighted pixels above the scaled region of interest shape.

19. The method of claim 13, the cardiac electrical signal feature comprising at least one of an activation time, a detected activation, a minimum voltage value, a maximum voltages value, a maximum negative time-derivative of voltage, an instantaneous potential, a voltage amplitude, a dominant frequency, and a peak-to-peak voltage.

* * * * *